US007312089B2

(12) United States Patent
Lee et al.

(10) Patent No.: US 7,312,089 B2
(45) Date of Patent: Dec. 25, 2007

(54) DETECTION OF ERYTHROPOIETIN AND ERYTHROPOIETIN RECEPTOR

(75) Inventors: Jong Y. Lee, 514 Huron Blvd., #A11, Minneapolis, MN (US) 55414; Mary S. Lee, Northbrook, IL (US); John S. Lee, Northbrook, IL (US)

(73) Assignee: Jong Y. Lee, Minneapolis, MN (US)

( * ) Notice: Subject to any disclaimer, the term of this patent is extended or adjusted under 35 U.S.C. 154(b) by 691 days.

(21) Appl. No.: 10/240,988

(22) PCT Filed: Apr. 5, 2001

(86) PCT No.: PCT/US01/11022

§ 371 (c)(1),
(2), (4) Date: Oct. 4, 2002

(87) PCT Pub. No.: WO01/77677

PCT Pub. Date: Oct. 18, 2001

(65) Prior Publication Data

US 2003/0180822 A1 Sep. 25, 2003

Related U.S. Application Data

(60) Provisional application No. 60/194,706, filed on Apr. 5, 2000.

(51) Int. Cl.
*G01N 33/563* (2006.01)

(52) U.S. Cl. .............. 436/512; 436/519; 436/524; 436/528; 436/165; 436/172; 436/809; 436/7.93; 436/7.94; 436/7.95; 436/334; 435/3; 435/7.1; 435/7.72; 435/7.92; 435/336; 435/343; 435/287.2

(58) Field of Classification Search ................. 435/1.1, 435/2, 3, 7.2, 7.25, 7.72, 7.9, 7.92–7.95, 435/334, 336, 343, 287.2; 436/510, 512, 436/519, 524, 528, 63, 165, 172, 808, 809
See application file for complete search history.

(56) References Cited

U.S. PATENT DOCUMENTS

| 5,712,370 | A | * | 1/1998 | Fibi et al. | 530/388.23 |
| 5,843,726 | A | * | 12/1998 | Lee | 435/69.7 |
| 5,885,574 | A | * | 3/1999 | Elliott | 424/133.1 |
| 6,153,190 | A | * | 11/2000 | Young et al. | 424/141.1 |

OTHER PUBLICATIONS

Noe et al., A sensitive sandwich ELISA for measuring erythropoietin in human serum, British Journal of Haematology, (Mar. 1992) vol. 80, No. 3, pp. 285-292.*
Kasai et al., Sensitive sandwich enzyme immunoassay for human Epo. Clin. Chem. Enzym. Comms. (1990), vol. 2: 137-143.*
Wognum et al., An enzyme-linked immunosorbent assay for erythropoietin using monoclonal antibodies, tetrameric immune complexes, and substrate amplification. Blood, (Aug. 1, 1989) vol. 74, No. 2, pp. 622-628.*
D'Andrea et al., Anti-erythropoietin receptor monoclonal antibodies Inhibit erythropoietin binding and neutralize bioactivity, Blood 82 (1): 46-52 (Jul. 1, 1993).*
Spirak, et al. Solid-Phase Binding Assay for Erythropoietin Antibodies. Proceedings of the Society for Experimental Biology and Medicine, 169, 406-412 (1982).

(Continued)

*Primary Examiner*—Gailene Rio-Gabel
(74) *Attorney, Agent, or Firm*—Cyr & Associates, P.A.

(57) ABSTRACT

The invention is based on the development of several sensitive and simple methods for detecting erythropoietin and the erythropoietin receptor and associated antibodies. The methods and reagents are useful for differential diagnosis in Epo and EpoR related clinical problems. Methods and kits for simultaneous measurement of erythropoietin and erythropoietin receptor in a biological sample are described.

19 Claims, 12 Drawing Sheets

OTHER PUBLICATIONS

Wognum, et al. An Enzyme-Linked Immunosorbent Assay for Erythropoietin Using Monoclonal antibodies, Tetrameric Immune, and Substrate Amplification. Blood, 72, 622-628 (1989).

Elliot et al. Activation of the Erythropoietin (EPO) Preceptor by Bivalent Anti-EPO Receptor Antibodies. Journal of Biological Chemistry, 271, 24691-24697.

* cited by examiner

MW
kDa 58.1 — ▬       EpoRex-th 39.8 ●

29.0 ● ▬ — ● Epo-bp
              GST 14.3 ●

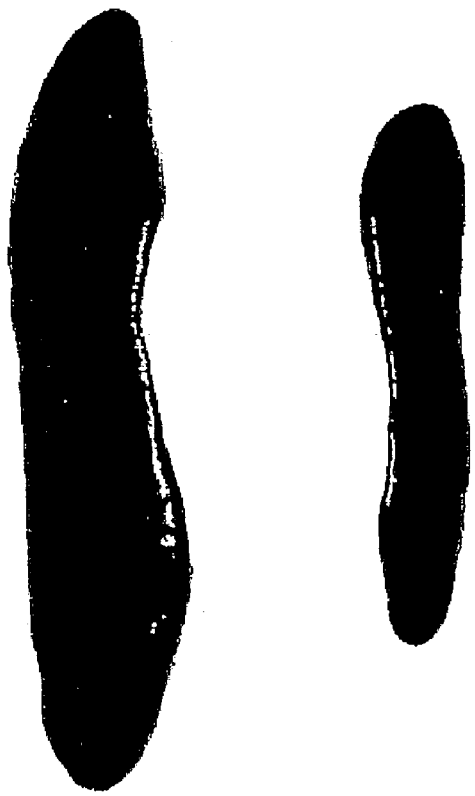
FIG. 7A  FIG. 7B  FIG. 7C  FIG. 7D  1 cm

DETECTION OF ERYTHROPOIETIN AND ERYTHROPOIETIN RECEPTOR

This application claims priority under 35 U.S.C. § 119(e) to U.S. provisional patent application Ser. No. 60/194,706, filed Apr. 5, 2000.

TECHNICAL FIELD

This invention relates to assays for simultaneous detection of erythropoietin (Epo) and erythropoietin-receptor (EpoR). In particular, immunoassays and PCR-based assays are described for simultaneously detecting Epo and EpoR, and related nucleic acids.

BACKGROUND OF THE INVENTION

Erythropoietin (Epo) is a glycoprotein hormone of molecular weight 34 kilodaltons (kDa) that is produced in the mammalian kidney and liver. Epo is a key component in erythropoiesis, inducing the proliferation and differentiation of red cell progenitors. Epo activity also is associated with the activation of a number of erythroid-specific genes, including globin and carbonic anhydrase. Bondurant et al., *Mol. Cell Biol.* 5: 675-683 (1985); Koury et al., *J. Cell. Physiol.* 126: 259-265 (1986). The erythropoietin receptor (EpoR) is a member of the hematopoietic/cytokine/growth factor receptor family, which includes several other growth factor receptors, such as the interleukin (IL)-3, -4 and -6 receptors, the granulocyte macrophage colony-stimulating factor (GM-CSF) receptor as well as the prolactin and growth hormone receptors. Bazan, *Proc. Natl. Acad. Sci USA* 87: 6934-6938 (1990). Members of the cytokine receptor family contain four conserved cysteine residues and a tryptophan-serine-X-tryptophan-serine motif positioned just outside the transmembrane region. The conserved sequences are thought to be involved in protein-protein interactions. Chiba et al., *Biochim. Biophys. Res. Comm;* 184: 485-490 (1992).

EpoR cDNA has been isolated recently from mouse liver (Tojo et al., *Biochem. Biophys. Res. Comm.* 148: 443-48 (1987)) and from human fetal liver. Jones et al., *Blood* 76: 31-35 (1990); Winkelmann et al., *Blood* 76: 24-30 (1990). The human cDNA encodes a polypeptide chain of MW ~55 kDa and having about 508 amino acids. Genomic clones of human EpoR have been isolated and sequenced. Penny and Forget, *Genomics* 11: 974-80 (1991); Noguchi et al., *Blood* 78: 2548-2556 (1991). Analysis of the coding sequence predicts about 24 amino acid residues in a signal peptide, about 226 amino acids in an extracellular domain, about 23 amino acids in a membrane-spanning domain, and about 235 amino acids in a cytoplasmic domain. D'Andrea and Zon, *J. Clin. Invest.* 86: 681-687 (1990); Jones et al., *Blood* 76: 31-35, (1990) and; Penny and Forget, *Genomics* 11: 974-80 (1991). The mature human EpoR protein has about 484 amino acids. All human erythroid progenitor cells have been shown to contain Epo receptors. Binding of Epo appears to decline as erythroid progenitor cells mature, until Epo receptors are not detectable on reticulocytes. Sawada et al., *J. Clin. Invest.* 80: 357-366 (1987); Sawada et al., *J. Cell. Physiol.* 137: 337 (1988). Epo maintains the cellular viability of the erythroid progenitor cells and allows them to proceed with mitosis and differentiation. Two major erythroid progenitors responsive to Epo are the Burst-forming units-erythroid (BFU-E) and the Colony-forming units-erythroid (CFU-E). The Epo receptor number correlates very well with the response to Epo in normal BFU-E and CFU-E. Epo receptor numbers appear to decline after reaching the peak receptor number at the CFU-E stage in human and murine cells. Sawada et al., *J. Clin. Invest.* 80: 357-366 (1987); and Landschulz et al., *Blood* 73: 1476-1486 (1989). The recovery of Epo receptors after removal of Epo appears to be dependent on protein synthesis, which suggests down-regulation of Epo receptor by degradation, and the subsequent upregulation of receptors by the new synthesis of receptors when Epo is removed. Sawyer and Hankins, *Blood* 72: 132 (1988); and Komatsu and Fujita, *Cancer Res.*, 53:1156-1161 (1993). Studies of Epo receptors on megakaryocytes and erythroid progenitors suggest that there is a link between the regulation of erythropoiesis and thrombopoiesis, in that stimulation of cell division by both cell types is controlled by Epo receptor numbers. Berridge et al., *Blood* 72: 970-977 (1988); and Komatsu and Fujita, supra. Although the Epo receptor has been cloned, the precise mechanisms involved in binding of Epo to Epo receptors and the relationship to subsequent erythropoietic processes are not known.

Characterization of the Epo receptor (EpoR) has been difficult due to the extremely small quantities of EpoR that can be obtained from natural sources. Thus, the mechanism of Epo interaction with its receptor, which stimulates erythropoiesis, is still unknown. D'Andrea and Zon, *J. Clin. Invest.* 86: 681-687 (1990). Recently this mechanism has been of great interest in understanding the role of growth factors and their receptors in leukemogenesis; altered hematopoietic growth factors and their receptors may contribute to tumorigenesis and leukemogenesis. Dunbar et al., *Science* 245: 1493-1496 (1989) and; Li et al., *J. Virol.* 57: 534-538 (1986).

Several studies of the correlation between the Epo responsiveness of a particular cell type and the affinity of the cell type for Epo have reported discordant results. These studies have used recombinant Epo or EpoR possessing some non-native amino acid sequence from the corresponding plasmid vectors. Berridge et al., *Blood* 72: 970-977 (1988); and Harris et al., *J. Biol. Chem.* 267: 15205-09 (1992). It is possible that tertiary structural changes and/or other features of these recombinant Epo or EpoR molecules have changed the characteristics of the native protein. Thus, it would be a significant advance to obtain substantially pure fragments of the Epo receptor, free of extraneous (e.g, vector) amino acid sequence. Although it could not be predicted whether or not such fragments would retain functional activity, nevertheless a purified extracellular domain fragment would be particularly useful since Epo binds to the extracellular domain of the Epo receptor.

SUMMARY OF THE INVENTION

The invention is based on the development of several sensitive and simple methods for detecting Epo or EpoR proteins and associated antibodies. The methods and reagents described herein represent useful tools for differential diagnosis in Epo and EpoR related clinical problems, as well as other hematological growth-factor-related clinical problems. Purification of pure human Epo-bp (Epo binding protein, i.e., the extracellular domain of EpoR) and antibodies thereto are benchmarks that allowed the present methods to be developed for therapeutic and diagnostic use. Visualization of Epo-R is possible now, both in vitro in human samples and in vivo in animal studies. The measurement of Epo or EpoR, and antibodies thereto, will help in understanding the structural and functional relationship in Epo/Epo-R interactions on blood cell progenitors.

The assay method(s) described herein are able to detect nano-concentrations of Epo and EpoR-soluble proteins in the human blood and tissue samples. Sensitive detection allows a better understanding of the Epo/EpoR interaction in blood cell production and related diseases in blood cell production. Thus, the present methods allow treatment methods to be established to control hematological malignancies and some systemic cardiovascular diseases.

In one aspect, the invention features a method for simultaneous measurement of Epo and EpoR in a biological sample. The method includes a) providing a solid substrate having first and second antibodies attached thereto in different, discrete regions, wherein the first antibody has specific binding affinity for Epo and the second antibody has specific binding affinity for EpoR, and wherein the first and second antibodies are functional antibody fragments (e.g., Fab fragments); and b) contacting the solid substrate with the biological sample under conditions wherein Epo and EpoR in the biological sample becomes bound to the first and the second antibodies. The presence, absence, or amount of Epo and EpoR is detected on the solid substrate. The first and second antibodies can be polyclonal antibodies.

Detecting the presence, absence, or amount of Epo and EpoR can include contacting the solid substrate of part b), above, with third and fourth antibodies, wherein the third antibody has specific binding affinity for Epo and the fourth antibody has specific binding affinity for EpoR, and wherein the third and fourth antibodies are detectably labeled. The third and fourth antibodies can be polyclonal antibodies.

Detecting the presence, absence, or amount of Epo and EpoR also can include d) contacting the solid substrate of part b), above, with third and fourth antibodies, wherein the third antibody has specific binding affinity for Epo and the fourth antibody has specific binding affinity for EpoR; and e) contacting the solid substrate of part d) with fifth labeled antibodies having specific binding affinity for the third and fourth antibodies. The third and fourth antibodies can be polyclonal antibodies. The fifth labeled antibodies can be labeled with an enzyme, a substrate, or a fluorescent moiety.

The invention also features a kit for detecting Epo and EpoR in a biological sample. The kit includes (a) a solid substrate (e.g., microtiter plate) having first and second antibodies attached thereto in different, discrete regions, wherein the first antibody has specific binding affinity for Epo and the second antibody has specific binding affinity for EpoR, and wherein the first and second antibodies are functional antibody fragments; (b) a first container having third antibodies enclosed therein, wherein the third antibodies have specific binding affinity for Epo; and (c) a second container having fourth antibodies enclosed therein, wherein the fourth antibodies have specific binding affinity for EpoR. The kit further can include a third container having control antigen enclosed therein. The kit also can include a label or package insert indicating that Epo and EpoR can be simultaneously detected by contacting the solid substrate with the biological sample under conditions wherein any Epo or EpoR in the biological sample becomes bound to the first and second antibodies and contacting the solid substrate with Epo or EpoR bound thereto with the third and the fourth antibodies. The first and second antibodies can be polyclonal antibodies and can be functional antibody fragments. The third and fourth antibodies can be polyclonal antibodies.

The invention also features a method for detecting the presence, absence, or amount of EpoR on human blood progenitor cells. The method includes contacting a biological sample such as blood or bone marrow with antibodies having specific binding affinity for EpoR, wherein the biological sample contains human blood progenitor cells, and wherein the contacting occurs under conditions wherein antibodies become bound to EpoR on the human blood progenitor cells in the biological sample, and detecting the presence, absence, or amount of EpoR by identifying the human blood progenitor cells having antibody bound thereto. The human blood progenitor cells can include megakaryocytes, erythroid, and myeloid progenitor cells.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 1 also depicts the recombinant fusion protein, EpoRex-th, that is expressed from pJYL26.

FIG. 4 is a Western blot showing binding of sheep anti-Epo-bp antibody to Epo-bp.

FIGS. 7A-7D are photographs of spleens isolated from rats treated with Epo (A-C) and from control rats (D).

FIGS. 8A-8C are of control cells at 100× magnification (8A and 8C) or at 400× magnification (8B). FIGS. 8D-8F are preimmune serum treated cells as positive controls (1000×). FIGS. 8C and 8F are fluorescein labeled, Fab-fractionated sheep serum treated cells. It is noted that the preimmune serum treated samples (8F) did not show any receptor binding activity as the same shown on control cells (C).

DETAILED DESCRIPTION OF THE INVENTION

Figure 1:
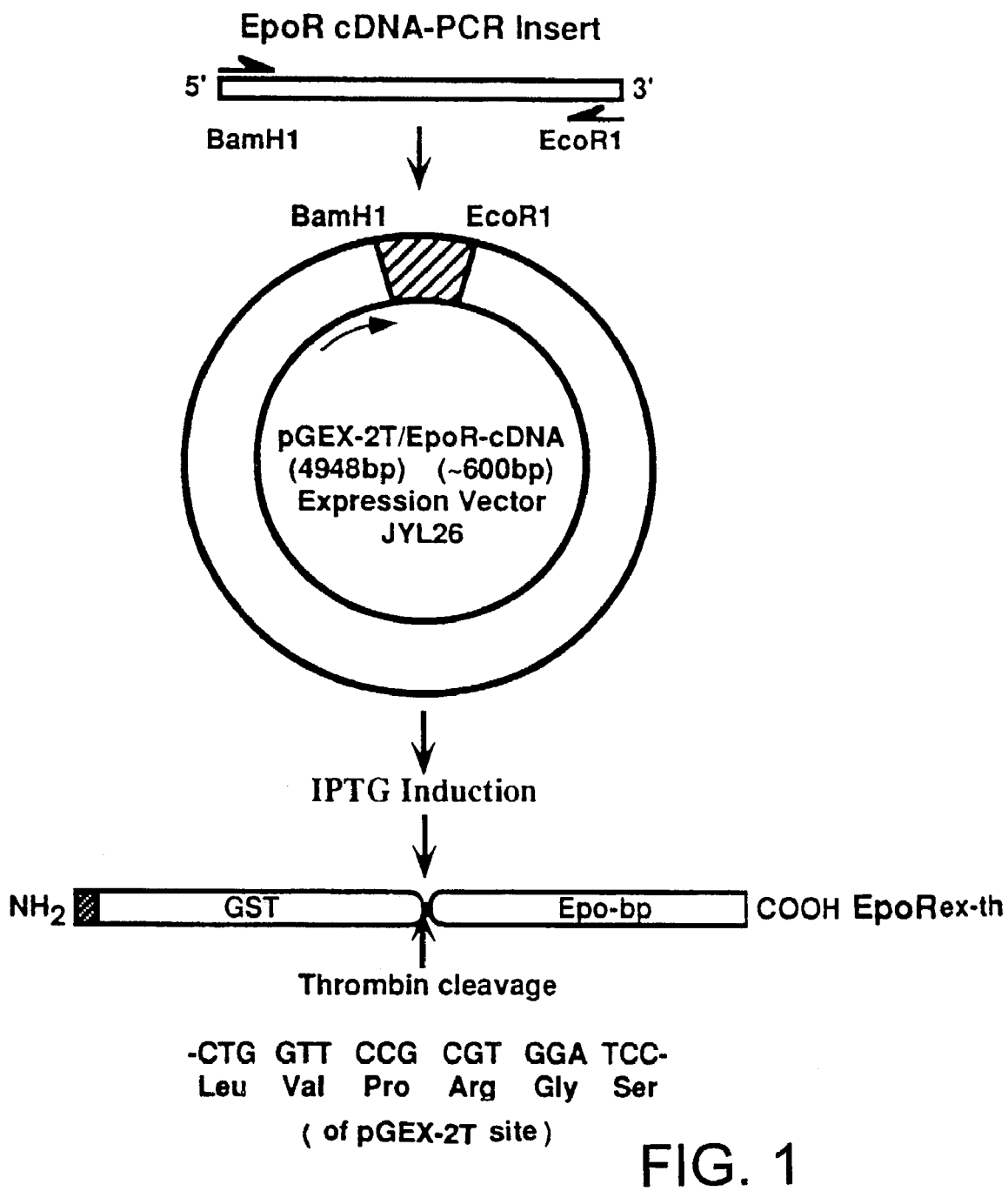
FIG. 1 is a diagrammatic representation of pJYL26, a plasmid having about 678 bp of the 5' coding sequence of human erythropoietin receptor cDNA inserted into the expression vector pGEX-2T.

Despite the availability of recombinant human Epo and full-length human Epo receptor cDNA clones, little is known about the interaction of Epo and EpoR, or the signal transducing mechanisms involved in proliferation and differentiation of erythroid progenitor cells.

Plasmid expression vectors permit expression of a protein from cloned coding sequences that have been inserted into the vector. Expression vectors generally have a selectable marker and a replication origin for selection and maintenance of the vector in a host cell, as well as inducible regulatory elements for inducing high level expression of a polypeptide suitable for fusing to an inserted gene. It is preferred that convenient restriction sites be engineered into the vector downstream from a proteolytic cleavage site sequence. A preferred polypeptide to be fused to the EpoR coding sequence fragment is glutathione S-transferase, possessing a thrombin proteolytic cleavage site at the carboxyl terminus.

An expression vector for the invention disclosed herein expresses the EpoR extracellular domain as part of a fusion protein that can subsequently be cleaved to yield purified EpoR extracellular domain. The coding sequence for the EpoR extracellular domain may be engineered in any manner suitable for inserting the sequence in the appropriate reading frame in the expression vector. For example, a pair of polymerase chain reaction (PCR) primers may be synthesized, such that the first primer corresponds to the coding sequence at the 5' end of the extracellular domain and the second primer is complementary to the coding sequence of the 3' end of the extracellular domain. The primers preferably have convenient restriction enzyme sites flanking the portions of the primers corresponding to the ends of the desired target sequences. The primers are used to amplify the EpoR extracellular domain from a full length human EpoR cDNA template. The resulting PCR product is then cloned into an expression vector. It is preferable to synthesize PCR primers having different restriction sites at each end, rather than the same restriction site. The presence of different restriction sites at each end of the PCR product facilitates the insertion of the human EpoR coding sequence fragment in the sense orientation.

High level expression of a fusion protein having human erythropoietin receptor extracellular domain as part of the fusion protein is achieved by inducing expression from the recombinant plasmid expression vector in a host cell culture. A fusion protein is hereinafter referred to as EpoRex-th and a purified human erythropoietin receptor extracellular domain hereinafter is referred to as Epo-bp (Epo-binding protein). A cell protein extract is preferably prepared from an expressing E. coli culture in any suitable manner. EpoRex-th may be purifed from the extract as desired. For example, the extract may be passed over a column having the ability to bind the portion of the fusion protein upstream of the Epo-bp coding sequence. The fusion protein will bind to the column, while other proteins in the extract are eluted in column washes with a buffer that allows binding of fusion protein to the column matrix. EpoRex-th can be subsequently eluted in high purity by changing the buffer conditions.

Purification of Epo-bp may be accomplished by cleaving purified EpoRex-th using an appropriate cleavage method. For example, the cleavage site between the upstream polypeptide and Epo-bp may be sensitive to cyanogen bromide or, alternatively, may be sensitive to site-specific protease cleavage. In a preferred embodiment, a thrombin proteolytic cleavage site is engineered into the upstream polypeptide, but 5' to the convenient restriction cloning sites positioned at the carboxyl terminus of the upstream polypeptide coding sequence.

The cleaved Epo-bp polypeptide segment may be separated from the upstream polypeptide segment by purification techniques such as size exclusion chromatography, isoelectric focusing, or affinity chromatography. Furthermore, more than one purification technique may be used, if desired, to achieve the appropriate degree of purification. A preferred purification technique is affinity chromatography. For example, a protease-treated fusion protein mixture may be applied to a column having agarose beads coupled to Epo. The cleaved Epo-bp segment will bind to the Epo-agarose, while the upstream polypeptide segment will pass through the column. Epo-bp may then be eluted by lowering the pH of the liquid phase.

In an embodiment of the invention, the coding sequence for amino acids 25 through 250 of human EpoR (hEpoR) is cloned into pGEX-2T (Pharmacia, Mechanicsburg, Pa.). pGEX-2T has an IPTG inducible promoter operably linked to a coding sequence for glutathione S-transferase (GST). The 3' end of the GST coding sequence has a thrombin proteolytic cleavage site in the correct reading frame, as well as convenient cloning sites for inserting a coding sequence to be covalently coupled to GST.

A PCR product having amino acids 25 through 250 of hEpoR is made from a suitable DNA template, for example a full-length human EpoR cDNA. A PCR primer is sythesized having the 5' end of the extracellular domain coding sequence as well as a BamH1 site, and a PCR primer is synthesized having sequence complementary to the 3' end of the extracellular domain coding sequence as well as an EcoR1 site. The BamH1 site in pGEX-2T is positioned 5' to the EcoR1 site relative to the GST coding sequence. The PCR product is cloned into pGEX-2T, and a transformed E. coli colony having a plasmid of the expected size is identified.

A fusion protein having an amino terminal GST segment and a carboxy terminal EpoR extracellular domain segment is expressed in transformed E. coli by inducing transcription with IPTG. IPTG derepresses the lac promoter positioned upstream of the fusion protein coding sequence. After allowing expression for a period of time sufficient to accumulate an amount of the fusion protein, cells are lysed and a crude extract is made in any suitable manner. The crude extract mixture has the fusion protein in addition to many other cellular proteins. The fusion protein, EpoRex-th, may be purified from the extract as desired.

In a preferred embodiment, EpoRex-th is passed over a column having agarose beads coupled to glutathione (GSH). GSH is a substrate for GST, and the GST segment of EpoRex-th will bind to the immobilized GSH with high affinity. Thus, the fusion protein becomes bound to the column, while virtually all other proteins in the extract will not bind. After washing, EpoRex-th may be eluted from the column by adding reduced GSH to the liquid phase.

In an embodiment of the invention, purified human erythropoietin receptor extracellular domain polypeptide may be made by digesting EpoRex-th with thrombin. The resulting digested mixture of GST and Epo-bp may then be applied to an Epo affinity column. The Epo-bp binds to its ligand, Epo, whereas GST passes through the column. Epo-bp may be eluted in purified form through use of an appropriate elution buffer, for example 0.1M glycine, pH 3.0.

Antibodies

Antibodies to human erythropoietin receptor extracellular domain can be made by presentation of a purified preparation of such a polypeptide to the immune system of an animal. For example, purified Epo-bp may be injected subcutaneously, intramuscularly or intraperitoneally into animals such as rats, mice, rabbits, goats, or sheep. Booster injections can be given at intervals, if desired. Circulating antibodies against Epo-bp are made by the immune system of the injected animal, and these antibodies can be collected from the blood, and, preferably, from serum. Anti-Epo-bp serum can be used to detect Epo-bp in various assay formats, such as Western blots, ELISA assays and the like. Epo-bp to be detected may be from, for example, a purified preparation of Epo-bp, a bacterial or eukaryotic cell extract, a eukaryotic cell from an in vitro cell culture, a serum sample, or even a tissue or cell biopsy taken from an individual. Anti-Epo-bp antibodies are expected to recognize the extracellular domain of intact human EpoR as well as Epo-bp. Monoclonal antibodies directed against Epo-bp can be made by methods known in the art. D'Andrea et al., *Blood,* 75: 874-80 (1990); U.S. Pat. No. 4,558,005; and Harlow and Lane, Antibodies—Lab Manual, Cold Spring Harbor Laboratory, 1988.

For example, as described herein, anti-Epo-bp and anti-Epo antibodies were developed in sheep by inoculating Epo-bp or synthetic Epo every three to four weeks for three months in sheep, then collecting serum for antibody purification. The polyclonal antibodies were further purified for the Fab fraction that was fluorescein labeled.

Antibodies directed against Epo-bp preferably have a specific binding affinity for the EpoR extracellular domain. For example, serum from an animal injected with purified Epo-bp should provide detectable binding to Epo-bp in Western blots when 10 μg of purified Epo-bp are electrophoresed in a polyacrylamide gel and exposed to a 1:2000 dilution of the anti-Epo-bp serum.

Antibody fragments having specific binding affinity for Epo or EpoR can be generated by known techniques. For example, such fragments include, but are not limited to, $F(ab')_2$ fragments that can be produced by pepsin digestion of the antibody molecule and Fab fragments that can be generated by reducing the disulfide bridges of F(ab')2 fragments. In general, purified immunoglobulins can be added to tubes containing immobilized papain and incubated at about 37° C. with agitation. Papain is in a phosphate digestion buffer containing cysteine hydrochloride. Solublized Fab fragments can be recovered using a separator tube and purified by protein A chromatography.

It should be noted that the sets of antibodies that are used in the assays (capture and detector antibodies) can be from the same or from different preparations of antibodies. For example, both the capture and detector antibodies can be purified from sheep, or the capture antibody can be purified from sheep while the detector antibody is purified from goat (or vice versa).

Methods for Measuring Epo and EpoR and Portions Thereof

Although Epo and EpoR have been cloned and many studies have been carried out, no methods are available to distinguish between Epo-related and EpoR-related clinical problems. Predictions that are made typically are based on deduced speculation with clinical symptoms and standard blood tests. Thus, a reliable test method for detecting Epo and EpoR is needed. The present methods are appropriate for use at the clinical site for both rapid and sensitive detection of relevant proteins and antibodies in different disease states. The methods of the invention can be used to detect the presence, absence, or amount of Epo and EpoR.

As described herein, a polymerase chain reaction (PCR) based method can be used for detecting Epo or EpoR, including Epo-bp. PCR refers to a procedure or technique in which target nucleic acids are amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in PCR Primer: A Laboratory Manual, Ed. by Dieffenbach, C. and Dveksler, G., Cold Spring Harbor Laboratory Press, 1995.

In the PCR based method, labeled substrate and antibodies can be used to detect ligand-binding sites and to measure Epo/EpoR mRNA productions. Primers used in the reaction can be chemically synthesized using standard techniques, based on the sequences encoding Epo and EpoR, which are known and described above. In some embodiments, biotinylated primers can be used. For example, PCR reactions can be performed under standard conditions using a digoxigenin labeled nucleotide and a biotinylated primer to generate PCR products that are biotinylated and that contain digoxigenin. The PCR products can be immobilized on a substrate such as a microtiter plate that is coated with streptavidin or avidin. Immobilization typically is performed by incubating the PCR product in the presence of the prepared substrate, for a suitable amount of time e.g., at about 37° C. for 30 minutes. Products are detected by addition of an anti-digoxigenin antibody or a fragment thereof. The anti-digoxigenin antibody can be conjugated to an enzyme such as horseradish peroxidase or alkaline phosphatase to facilitate easy detection of products. In general, a peroxoidase substrate such as diaminobenzidine or a phosphatase substrate such as 4-methylumberlliferyl phosphate (MUP) or disodium p-nitrophenyl phosphate (NPP), is added to the reacted sample and color development is monitored visually, spectrophotometrically at 405 nm when NPP is used as the substrate, or spectrofluorometrically with a 365 nm excitation filter and a 450 nm emission filter when MUP is the substrate. Chemiluminescent detection of the PCR products also can be performed with a chemiluminescent substrate such as Luminol.

Another method for measuring Epo or EpoR including Epo-bp is an immunofluorescent labeling method. This method includes coating capture anti-Epo-bp fragments and anti-Epo fragments onto a substrate (e.g., microtiter plate) in different discrete regions. Typically, the antibody fragments are coated onto a substrate by incubating the antibody fragments with the substrate for about two hours at room temperature. A biological sample such as serum/plasma, homogenized tissue, or cells, including blood and bone marrow cells, are added to the coated substrate and incubated for a suitable amount of time. For example, the samples can be incubated for about 20-30 minutes at temperatures of about 24° C. to about 37° C. Fluorescently labeled detector antibodies (i.e., labeled anti-Epo and anti-EpoR antibodies) then are added, and the materials are incubated for a suitable amount of time (e.g., 10 to 30 minutes at 37° C.). The samples can be washed in an appropriate buffer such as 20 mM phosphate-buffered saline (PBS) with or without albumin. Positive samples can be identified by observation under a fluorescent microscope or by determining the absorbance at 405 nm using a microplate fluorometer.

The immunofluorescent labeling method also can be used to detect anti-Epo antibodies and anti-EpoR antibodies. To detect antibodies, the substrate is coated with Epo and EpoR (antigen) in different, discrete regions using the same method as described above. Sample is added, and fluorescently labeled antigen is added. Positive samples are identified in the same manner as for detecting Epo and EpoR.

Suitable fluorescent labels include, for example, fluorescein, 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, phycoerythrin (B-, R-, or cyanine-), allophycocyanin, Oregon Green™, and Cascade™ blue acetylazide (Molecular Probes, Inc., Eugene, Oreg.).

An additional method for detecting Epo or EpoR, including Epo-bp, is an enzyme immunoassay. The method includes use of magnetic separation, a technique that is highly efficient and specific for tissue typing, cell sorting, subcellular organelle fractionation, and DNA separation. Sensitivity of this method is expected to be 1000-fold enhanced when compared with the other methods available on the market, including the ELISA method. Epo and EpoR or Epo-bp, or anti-Epo antibodies and anti-EpoR antibodies can be detected in this method. In general, capture beads, e.g., agarose beads, are prepared by coating with either Epo or EpoR or a portion thereof for detecting anti-Epo or anti EpoR antibodies, or with anti-Epo or anti-EpoR antibodies for detecting Epo or EpoR. A biological sample is applied to the capture beads and incubated at an appropriate temperature and for an appropriate length of time, e.g., room temperature for about 25 minutes. Then, a species-specific, secondary antibody conjugated to an enzyme is added. After incubation and washing, enzyme substrate is added and color is developed. Beads can be pelleted and color is detected as described above.

Numerous variations of these methods can be performed. For example, detector antibodies can be biotinylated such that positive samples can be detected by addition of streptavidin or avidin conjugated to an enzyme and color development. Horseradish peroxidase conjugated molecules also will catalyze the oxidation of Luminol and light can be detected via chemiluminescence. The emission of light can be enhanced by inclusion of chemical enhancers.

The purified extracellular domain of EpoR disclosed herein is the first such pure human Epo receptor fragment (i.e., free of non-human or non-Epo receptor amino acid sequence) to be obtained. The experiments disclosed herein demonstrate that such a fragment retains the ability to specifically bind human Epo. The proteins and antibodies disclosed herein are useful for understanding the mechanisms of Epo-Epo receptor interaction. The purified Epo-bp of the present invention is also useful for investigating the structure of the Epo receptor and for identifying factors involved in regulating differentiation and proliferation mechanisms in erythroid progenitor cells. Moreover, the invention disclosed herein is useful for identifying and quantitating Epo and Epo receptor, as well as in understanding hematopoietic malignancy and certain cardiovascular system disorders. In addition, a major discovery described herein is that all human progenitor blood cells have been shown to contain Epo receptors and are able to binding Epo.

The invention will be further understood with reference to the following illustrative embodiments, which are purely exemplary, and should not be taken as limiting the true scope of the present invention as described in the claims.

EXAMPLES

Example 1

Materials and Methods

Glutathione (GSH)-agarose, pGEX-2T expression vector and Sephadex G-50 were purchased from Pharmacia (Mechanicsburg, Pa.). PCR reagents were from Perkin-Elmer Cetus (Norwalk, Conn.) and Affigel 15 was from BioRad (Richmond, Calif.). Bacteriophage T4 DNA ligase, restriction enzymes and isopropylthio-.beta.-D-galactoside (IPTG) were purchased from BRL Gibco (Gaithersburg, Md.). Geneclean II was from Bio 101, La Jolla, Calif. Nitrocellulose was from Schleicher & Schuell Co. (Keene, N.H.). Chemiluminescence (ECL) reagents and $^{125}$I-Epo were from Amersham (Arlington Heights, Ill.) and unlabeled Epo was a gift of Chugai-Upjohn (Rosemont, Ill.). Phenylmethylsulfonylfluoride (PMSF), diisopropylfluorophosphate (DFP), thrombin, trypsin and Triton X-100, were from Sigma Chemical Company (St. Louis, Mo.). Biotinylated rabbit anti-sheep antibodies and avidin-horseradish peroxidase were from Pierce Co. (Rockford, Ill.). LAP37, a full-length human erythropoietin receptor (EpoR) cDNA preparation, was provided by Dr. Bernard G. Forget, Yale University, New Haven, Conn. All other chemicals were of reagent grade.

Example 2

Construction of EpoR cDNA Recombinant Vector

A recombinant plasmid expression vector, pJYL26, was constructed from a PCR product having the human Epo receptor extracellular domain coding sequence and from the plasmid vector pGEX-2T. The construction of this plasmid is explained below.

PCR amplification was carried out using a full-length human EpoR cDNA, LAP37, as a template. The 5'-sense primer was 5'-TTGGATCCGCGCCCCCGCCTAAC-3' (SEQ ID NO: 1). This primer has a BamH1 linker sequence at the 5' end, followed by the coding sequence for amino acids 25 through 29 of the full length human EpoR protein. The 3'-antisense primer was 5'-TGAATTCGGGGTCCAG-GTCGCT-3' (SEQ ID NO: 2). This primer has an EcoR1 linker followed by sequence complementary to the coding sequence for amino acids 226 through 222 of full length EpoR. Using a Perkin Elmer-Cetus PCR kit, PCR was carried out with 0.1 µg of LAP37 cDNA, 20 pM of each primer, 1.25 mM dNTP mixture (dGTP, dCTP, dTTP and dATP), 0.5 µl of Taq polymerase, and 10× buffer supplied in the PCR kit. Amplification was carried out by a PTC-100 Programmable Thermal Controller, (M. J. Research, Inc. Watertown, Mass.), with denaturation at 94° C. for 1 min, annealing at 55° C. for 1 min and extension at 72° C. for 1½ min, repeated for 25 cycles.

The sizes of the PCR product (~600 bp) and pGEX-2T (~4.9 kb) were verified on 1% Seakem and 2% Nusieve agarose (FMC Bioproducts, Rockland, Me.) gels running in 1×TA buffer (50×TA in 1 liter volume containing 242 g Tris-base and 57.1 ml acetic acid), with a Hae III standard. Both the PCR product and pGEX-2T were purified from gel slices by the Geneclean II method as described by the manufacturer (Bio 101, La Jolla, Calif.). Concentrations of the PCR product and pGEX-2T were estimated by absorbance readings at OD260. Both DNAs were then digested with BamH1 and EcoR1 for 4 hours at 37° C. before ligation. The digested products were analyzed on 1% Seakem and 2% Nusieve agarose gels. Both the PCR product and pGEX-2T fragments were cut from the gel and purified again by the Geneclean II method.

The ligation was done in a mixture having 1 µg/µl each of PCR product and pGEX-2T. The mixture was incubated at 45° C. for 5 minutes and chilled to 0° C. Then, in a 10 µl final volume, 1 µl each of 10× bacteriophage T4 DNA buffer and 10× bacteriophage DNA ligase, and 10 mM ATP were added. The whole mixture was then incubated at 16° C. in a circulating water bath overnight. Productive ligation was verified by electrophoresis in a 1% agarose gel in 1×TA buffer running at 100 volts with lanes containing size standards, pGEX-2T, PCR product, and the ligated product (PCR product+pGEX-2T). The ligated product was verified to be ~5.5 kb. An aliquot of ligation mixture was then transformed into E. coli strain JM109 (20 µg ligation mixture/200 µl JM109). For the transformation, the E. coli mixture was incubated on ice for 30 minutes after mixing gently by inverting, and incubated at 42° C. exactly 90 seconds. Then the mixture was chilled on ice for 1-2 minutes and 500 µl LB medium (for 1 liter, 10 g bacto-tryptone, 5 g bacto-yeast and 10 g NaCl, pH 7.5, autoclave) was added. After incubating at 37° C. for 45 minutes, the LB mixtures were spread on LB/Amp agar petri plates in amounts of 50, 75, 125, 150, and 300 ml of LB mixture. Agar petri plates were prepared with 20-30 ml of LB/Amp medium, containing 15 g agar/liter LB (autoclaved) and 100 µg/liter ampicillin. Control LB/Amp plates were made with intact pGEX-2T, digested pGEX-2T and PCR product only. The plates were kept on the bench top to absorb liquid for a few hours and inverted plates were incubated at 37° C. for 24 hours. Grown colonies were seeded on gridded plates, which were incubated again at 37° C. for 24 hours, while another set of all colonies was grown in 5 ml each of the LB/Amp medium overnight.

The DNA was extracted from each colony by the miniprep method. Each colony was cultured overnight with 5 ml LB/Amp medium (2 µl/ml of 50 µg/ml Amp stock) in a loosely capped 15-ml plastic tube in a vigorously shaking 37° C. incubator. The following day, 1.5 ml of each culture was pelleted in a microfuge for 3 minutes at 4° C. at 14,000×g, and resuspended in 93 µl STET plus 17 µl of lysozyme stock (STET: 5% sucrose+5% Triton X-100+50 mM Tris, pH 8.0+50 mM EDTA, pH 8.0, stored at 4° C.; lysozyme stock: 5 mg/ml, stored in a freezer). The resuspended mixture was then incubated for 10 minutes at room temperature and boiled for 2 minutes before spinning in a microfuge at 4° C. for 15 minutes at 14,000×g. The pellet was removed with a sterile tooth pick, 2 µl of RNAse (100 mg/ml) was added to the supernatant, followed by incubation at 37° C. for 30 minutes. After incubation, 110 µl of ice-cold isopropanol was added and the mixture was inverted 4 times before pelleting at 14,000×g, 4° C. for 15 minute. The pellet (DNA) was then washed with ~1 ml of 70% ethanol to remove residual STET and other contaminants, and the pellet centrifuged again at 14,000×g, 4° C. for 15 minutes. The pellet was then air dried for 1-2 hours and resuspended in 25 µl of sterile dH$_2$O.

The extracted DNAs were verified on a 0.8% agarose gel in TA buffer, running at 100 volts until the front dye line migrated ⅘ of the length of the gel. The gel was stained with ethidium bromide (0.5 µg/ml) at room temperature for 15 minutes on a gentle shaker and destained with dH$_2$O for 15 minutes. DNA bands were examined under UV light. Cultures having DNA of the expected size were examined in 1% agarose gels running in TA buffer after EcoR1 and/or EcoR1 plus BamH1 digestion. The EcoR1 and BamH1 digestion was done by incubating the sample mixture at 37° C. water bath for 2 hours with the mixture of 1 µg of EcoR1 or BamH1 per 2 µg of DNA in 1 µl/10 µl sample volume of 10× reaction buffer provided in the restriction enzyme kit. One colony having a plasmid of about 5.5 kb in size was selected after examining both EcoR1 and EcoR1 plus BamH1 digested DNA sizes in 1% agarose gels. The plasmid in this colony was named pJYL26. A diagram of pJYL26 is shown in the upper part of FIG. 1.

Example 3

Purification of EpoRex-th Fusion Protein

This example teaches the production and purification of a fusion protein having two segments. The first segment is a polypeptide, GST, with a thrombin cleavage site at the carboxyl terminus. The second segment, fused to the first segment at the thrombin cleavage site, is the extracellular domain of human Epo receptor. The fusion protein EpoRex-th, containing GST and Epo-bp, is purified by GSH-agarose affinity chromatography.

Transformed E. coli containing the recombinant vector pJYL26 were grown overnight at 37° C. with vigorous shaking in 400 ml of LB medium with 100 µg/ml of ampicillin. The following day, the culture was diluted in 4 liters of fresh LB/Amp media and incubated for another 90 min before adding 1 mM isopropylthio-β-D-galactoside (IPTG). After 4 hours of IPTG induction, the cells were pelleted at 3,000×g at 4° C. for 15 min and resuspended in 160 ml of lysis buffer, containing 50 mM sodium phosphate, pH 7.4, 10 mM β-mercaptoethanol (βME), 10 mM EDTA, pH 8.0, 1 mM PMSF and 1 mM DFP. 160 mg of solid lysozyme was then added. Using a 60 cc syringe, the lysed cell suspension was homogenized by passing through 18, 21 and 23 gauge needles three times, and incubated on ice 30 min. After dry ice/methanol freeze thaw at 37° C. for 3 times and mild sonication, 1% of Triton X-100 was added. The supernatant was collected by centrifugation 15×kg at 4° C. for 15 min.

Figure 2A:
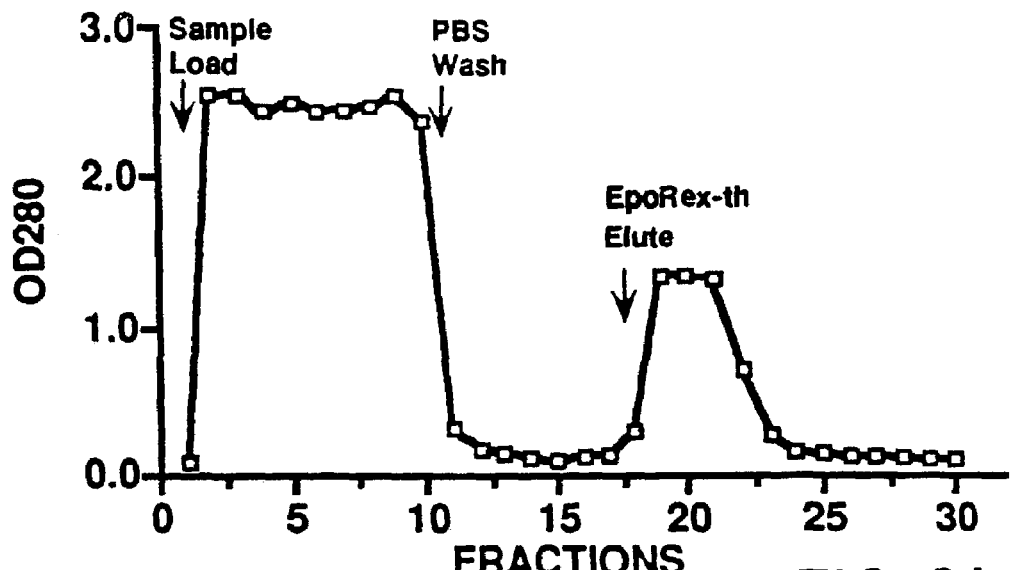
FIG. 2A shows the absorbance at 280 nanometers ($A_{280}$) of fractions collected from purification of an *E. coli* cell extract, expressing EpoRex-th, on a glutathione affinity column.
Figure 2B:
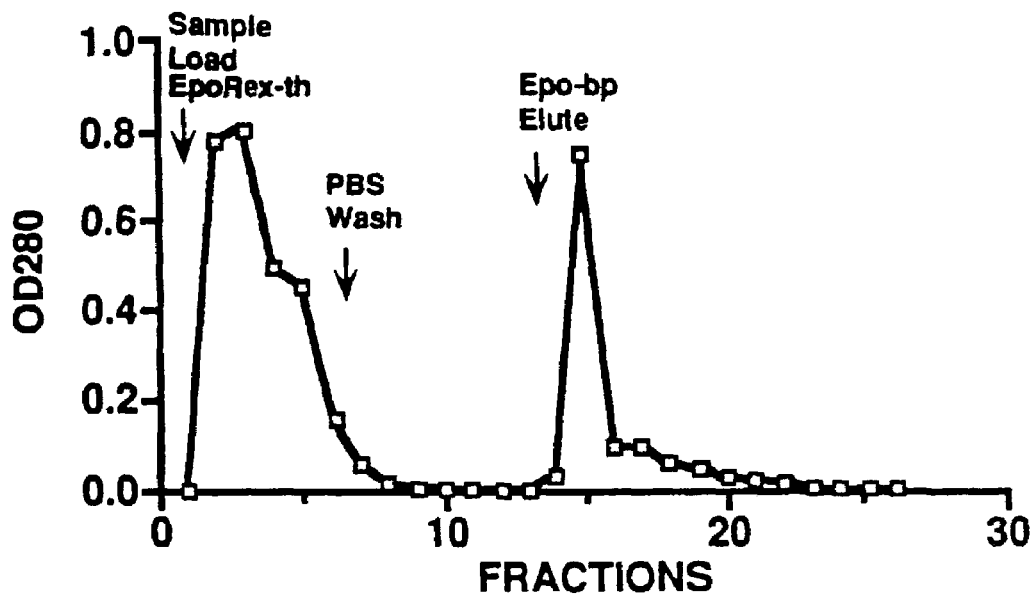
FIG. 2B shows the $A_{280}$ of fractions containing Epo-bp collected as a result of erythiopoietin affinity chromatography of thrombin treated EpoRex-th.

A GSH-agarose column was prepared by washing swollen GSH-agarose beads 3 times with 10 bed volumes of phosphate-buffered saline (PBS: 16 mM Na$_2$HPO$_4$, 4 mM NaH$_2$PO$_4$, pH 7.4 in excess salt of 3M NaCl) to remove preservatives and elutable dextran from the agarose. The column was then equilibrated with 5 bed volumes of isotonic PBS. The IPTG induced extract was applied to the column and the column was washed twice with 5 bed volumes of PBS, which elutes all proteins with no affinity for GSH-agarose EpoRex-th was then eluted by adding 5 bed volumes of elution buffer, containing 5 mM reduced GSH in 50 mM Tris-HCl, pH 8.0. Fractions of 1.0 ml were collected and the A$_{280}$ was determined for each fraction. FIG. 2a shows the A$_{280}$ data. Fractions 18-23 were subsequently shown to have the EpoRex-th protein. These fractions were pooled. From a four-liter cell culture preparation, an average of 2 mg of EpoRex-th was extracted.

Example 4

Purification of Epo-bp

EpoRex-th contains a thrombin-specific proteolytic cleavage site, as diagrammed in the lower half of FIG. 1. Thrombin cleaves specifically at the sequence -CTG GTT CCG CGT GGA TCC- (SEQ ID NO: 3), which codes for the amino acids Leu Val Pro Arg Gly Ser, as shown in FIG. 1. Smith and Johnson, Gene 67: 31-40 (1988). Thrombin was incubated with EpoRex-th to cleave the GST segment from the Epo-bp segment and the two segments were purified by Epo-agarose affinity, as described below.

Figure 3:
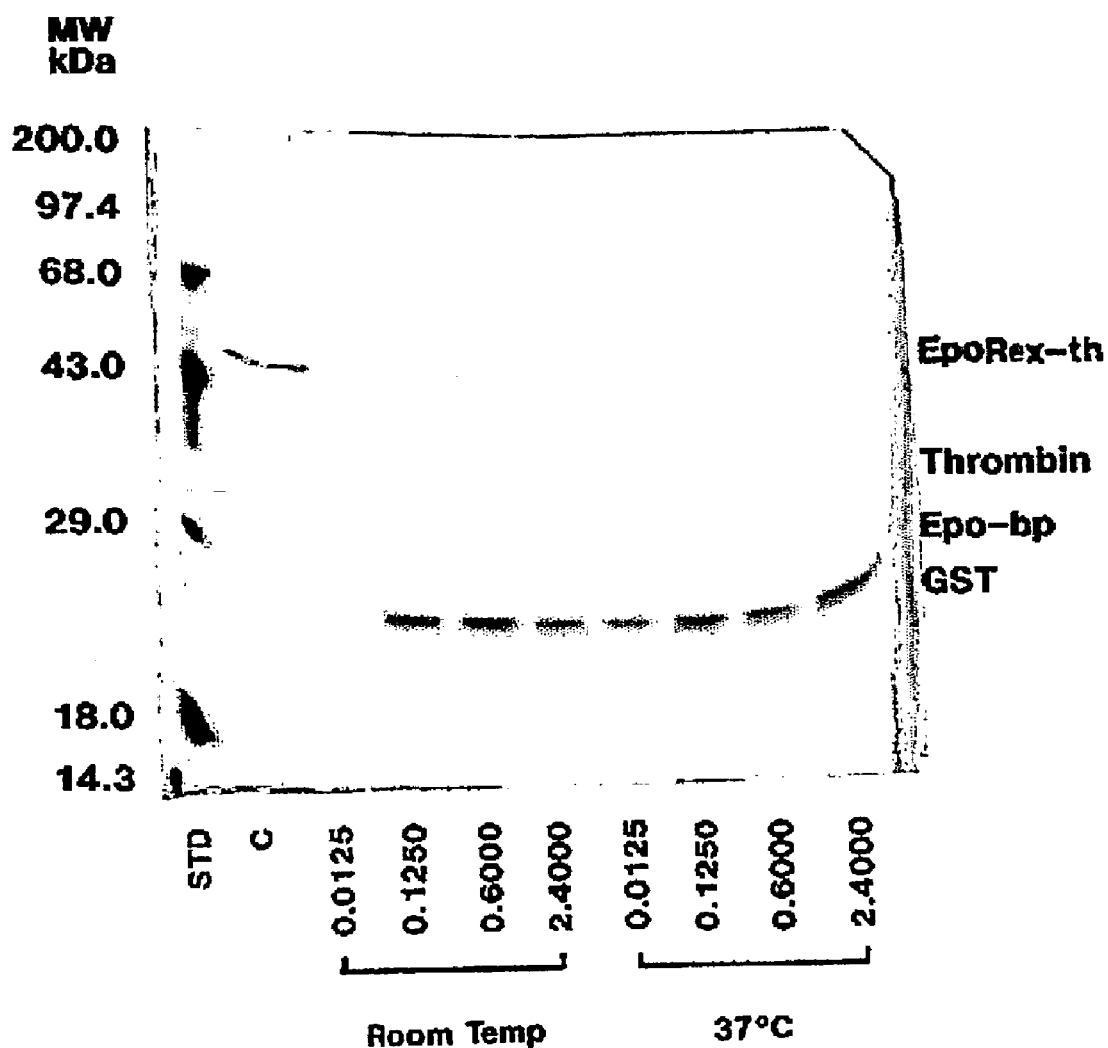
FIG. 3 is a photograph of a Coomassie blue stained polyacrylamide gel, showing the cleavage of EpoRex-th by thrombin.

Various thrombin concentrations were tested in order to find the most effective range of thrombin cleavage. Purified EpoRex-th was incubated with 0.0125, 0.125, 0.6 or 2.4 μg of thrombin per 60 μg EpoRex-th at room temperature or 37° C. for 1 hour in PBS buffer, pH 7.4. The results were analyzed by polyacrylamide gel (12.5%) electrophoresis. After staining with Coomassie blue, bands could be seen corresponding to the fusion protein EpoRex-th (55 kDa), Epo-bp (29 kDa) and GST (26 kDa). The 0.6 μg concentration was selected for complete digestion of EpoRex-th. The results are presented in FIG. 3.

For thrombin cleavage, 60 μg of EpoRex-th was incubated at room temperature for 1 hr with 0.6 μg thrombin. The mixture was applied to an erythropoietin-agarose column in Tris buffered saline (TBS) or PBS. Epo-bp was eluted with 0.1M glycine buffer, pH 3.0. Fractions of 0.5 ml were collected into tubes, containing 0.5 ml of 2M Tris-HCl, pH 7.5. Epo-bp peak fractions 14-19 were pooled and then dialyzed overnight in TBS or PBS at 4° C. for further experiments. Approximately 200 μg Epo-bp was extracted, starting from a four-liter cell culture preparation.

The Epo-agarose column was prepared from Epo-agarose beads. The Epo-agarose beads were prepared by overnight dialysis of Epo (0.5 mg/ml) in 0.1M 3 (N-morpholino)-propanesulfonic acid (MOPS) at 4° C. Epo was linked to Affigel 15 beads by admixing 1 ml of the dialyzed Epo-solution and 2 ml of washed Affigel 15, and incubated at room temperature for 2 hours on a rotating shaker. The supernatant was removed after microcentrifuging at 2000×g for 30 sec. The packed Epo-agarose beads were washed 3 times in TBS or PBS at 4° C. and stored until ready to use. After collecting desired protein fractions, Epo-agarose beads may be washed extensively with TBS or PBS and stored at 4° C. or reuse.

Example 5

Production of Antibodies to Epo-bp

This example teaches the production of antibodies directed against purified Epo-bp. Purified Epo-bp is electrophoresed in a 12.5% SDS-PAGE gel and the Epo-bp protein band is resuspended in PBS and injected into sheep. Sheep serum having anti-Epo-bp antibody is shown to detect purified human Epo-bp when the serum is diluted 1:2000.

Epo-bp (0.5 mg), purified as described above, was mixed with 2× treatment (Laemmli) buffer and boiled for 10 minutes. The mixture was applied to a 12.5% SDS gel and electrophoresed at 200 volts for 3-4 hours. The gel was stained with 0.125% Coomassie blue overnight, destained 1-2 hours with dH$_2$O, and the Epo-bp band cut out of the gel with a razor blade.

The Epo-bp gel slice was resuspended in 10-15 ml of PBS buffer and passed through a syringe repeatedly until the gel was crushed into small pieces forming a suspension mixture with PBS. The suspension was injected subcutaneously in adult sheep. Epo-bp was injected at a ratio of 0.5 mg Epo-bp or more per 25 kg weight of the animal. Two booster injections, with the same dose as in the initial injection, were given once every 3 weeks following initial injection. After the second booster injection, blood can be withdrawn for collection of antibodies. Injections can be given every month to maintain antibody production by the animal. Injection sites are rotated on the animal. Sambrook et al., Molecular Cloning 2nd Ed., Cold Spring Harbor Laboratory Press, Chapter 18, 1989.

To obtain blood from injected animals, hair at the blood sampling site was cleaned with 70% alcohol. Ear arteries or other accessible arteries were shaved. Sheep can be bled via the jugular vein using gravity withdrawal in a vacuumed bottle, and serum is separated. A small amount of xylene was applied to the tip of the ear but not at the bleeding site. Blood was gently withdrawn with a butterfly and put into a glass tube having no heparin. The blood was incubated at room temperature for 1 hour to allow clotting, the clot was loosened from the tube wall with a pasteur pipet, and the tube was incubated at 4° C. overnight. The clotted blood mixture was poured into a dish and the clot removed. The unclotted remainder was returned to the glass tube and centrifuged at 3000 rpm for 10 minutes. The supernatant (serum) was applied to an Epo-bp-affinity column and antibodies binding to the column were eluted by with 0.1M glycine buffer, pH 3.0, using the same procedures as discussed above for purification of Epo-bp. The eluate was dialyzed in PBS overnight at 4° C. and stored at −70° C. in 500 μl aliquots. The Epo-bp affinity column was prepared from Epo-bp and Affigel 15 agarose beads in the same manner as the Epo-bp Affigel beads described in Example 6 below.

Solutions used in this example are prepared as follows: Lysis Buffer II: 50 mM NaPO$_4$ (7.74 ml of 0.5M dibasic PO$_4$ plus 2.26 of 0.5M monobasic PO$_4$)+10 mM β-mercaptoethanol+10 mM EDTA, pH 8; PBS Buffer: 0.15M NaCl+16 mM dibasic PO$_4$+6 mM monobasic PO$_4$, pH 7.4; TBS buffer: for 1 liter, 12.5 ml of 2M Tris-HCl, pH 7.4+27.5 ml of 5M NaCl; 2× Treatment (Laemmli) buffer: 0.125M Tris-HCl, pH 6.8+4% SDS+20% glycerol+10% β-mercaptoethanol.

Sheep anti-Epo-bp serum was analyzed for binding to purified Epo-bp by Western blotting as described in Sambrook et al., Molecular Cloning, 2nd Ed., Cold Spring Harbor Laboratory Press, 1989 and in Western blotting protocols provided by the ECL manufacturer, Amersham Co., Arlington Heights, Ill. Following thrombin cleavage, EpoRex-th and Epo-bp were separated electrophoretically on an SDS-PAGE gel. The gel was then blotted onto nitrocellulose (Schleicher and Schuell Co., Keene, N.H.). Sheep anti-Epo-bp serum was added to the nitrocellulose in Blotto (for 1 liter: 80 g non-fat dry milk, 30 ml 5M NaCl, 10 ml 2M Tris-HCl, pH 7.5 and 0.05% Tween-20) at a 1:2000 dilution and incubated at room temperature for 1 hour with gentle agitation. After rinsing off the first antibody, a second reagent, biotinylated rabbit anti-immunoglobulin anti-sheep (1:10,000 dilution) antibody was added to the nitrocellulose in Blotto, and incubated at room temperature for another 1 hour with rocking. Horseradish peroxidase-avidin (1:10,000 dilution) was added and the mixture incubated at room temperature for 45 min. After soaking the washed nitrocellulose briefly in chemiluminescence (ECL) reagents, wet blots were exposed immediately on KODAK X-ray film. FIG. 4 shows a photograph of the Western blot, with the lanes having the following proteins applied: Lane 1, molecular weight standards; Lane 2, thrombin digested EpoRex-th; Lane 3, GST; Lane 4, purified Epo-bp. As shown in lane 4 of FIG. 4, purified Epo-bp was detected by a 1:2000 dilution of anti-Epo-bp antibody. The apparent molecular weight of the purified Epo-bp was about 29 kDa.

Example 6

Binding of Epo to Epo-bp

Ligand binding of Epo to Epo-bp and effects of Epo concentration on binding are taught in this example.

Epo-bp beads were prepared by adding 60 µg/ml Epo-bp to washed Affigel 15 agarose beads in PBS, with a final concentration of approximately 30 µg of protein per 1 ml of Epo-bp beads. The mixture was incubated at room temperature for 2 hours on a rotating platform. After washing 3 times with ice cold PBS buffer, the pellet was resuspended in 1 ml of PBS buffer. For binding assays, 30 µl of the final suspension (approximately 1.0 µg of Epo-bp) were admixed with various concentrations of $^{125}$I-Epo and incubated for 1 hour at room temperature while resuspending every 5 min with a pipet. At the end of the incubation, 1 ml of ice cold PBS buffer was added to wash out unreacted $^{125}$I-Epo and the wash was repeated twice more. The reacted beads were counted by a gamma counter. Proteins smaller than the intact Epo-bp from trypsin digested extracts (see below) were also applied in the same way to test any effect on ligand binding. Nonspecific binding was measured by the same method except the mixture was preincubated with a 200-fold excess of unlabeled Epo for 1 hour prior to adding labeled Epo.

Figure 5:
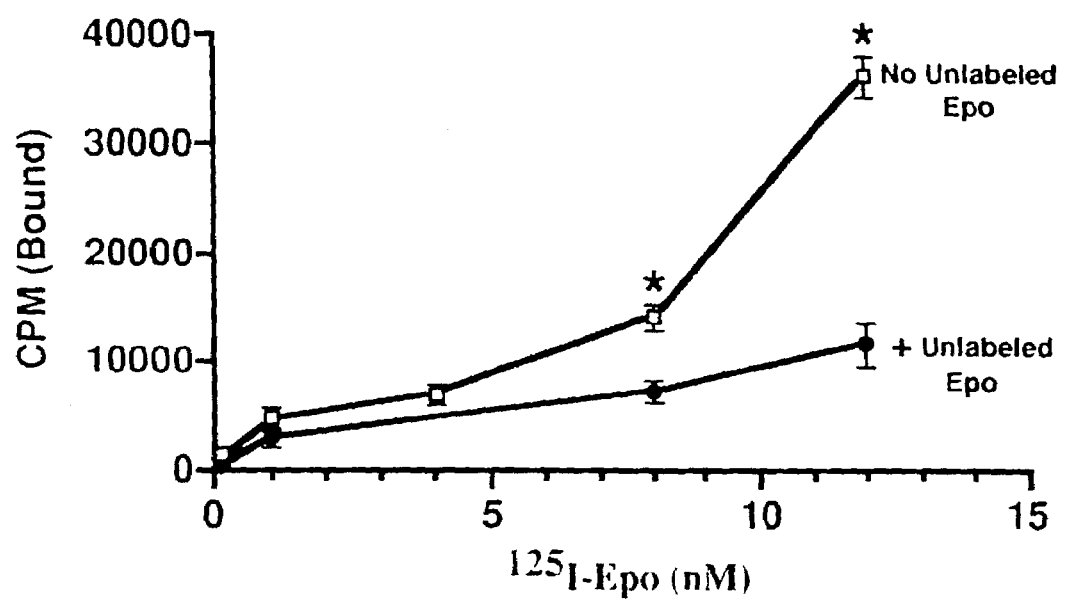
FIG. 5 shows the binding of various concentrations of human $^{125}$I-Epo to Epo bp, in the presence and absence of unlabeled Epo.

Binding of Epo-bp to Epo is shown in FIG. 5. Each point in FIG. 5 is the mean of 2-4 samples. Data are expressed as mean±SEM. A p value of less than 0.05 was considered significant. Results were analysed with the two-tailed Student t-test. The specific binding activity of Epo to Epo-bp dramatically increased as Epo concentration increased; the binding tripled from 8 nM to 12 nM $^{125}$I-Epo. Apparent saturation of Epo binding occurred at 12 nM. This was also confirmed in the unreacted supernatant of $^{125}$I-Epo. Binding of $^{125}$I-Epo to Epo-bp was significantly inhibited in the presence of unlabeled Epo at concentrations of 8 nM and higher of $^{125}$I-Epo (p<0.0001 in both comparisons). Nonspecific binding was somewhat higher than expected. It had been expected that the excess unlabeled Epo might eliminate $^{125}$I-Epo binding completely because of the sensitivity and specificity of Epo binding to Epo-bp shown in Western blots and binding assays.

Figure 6:
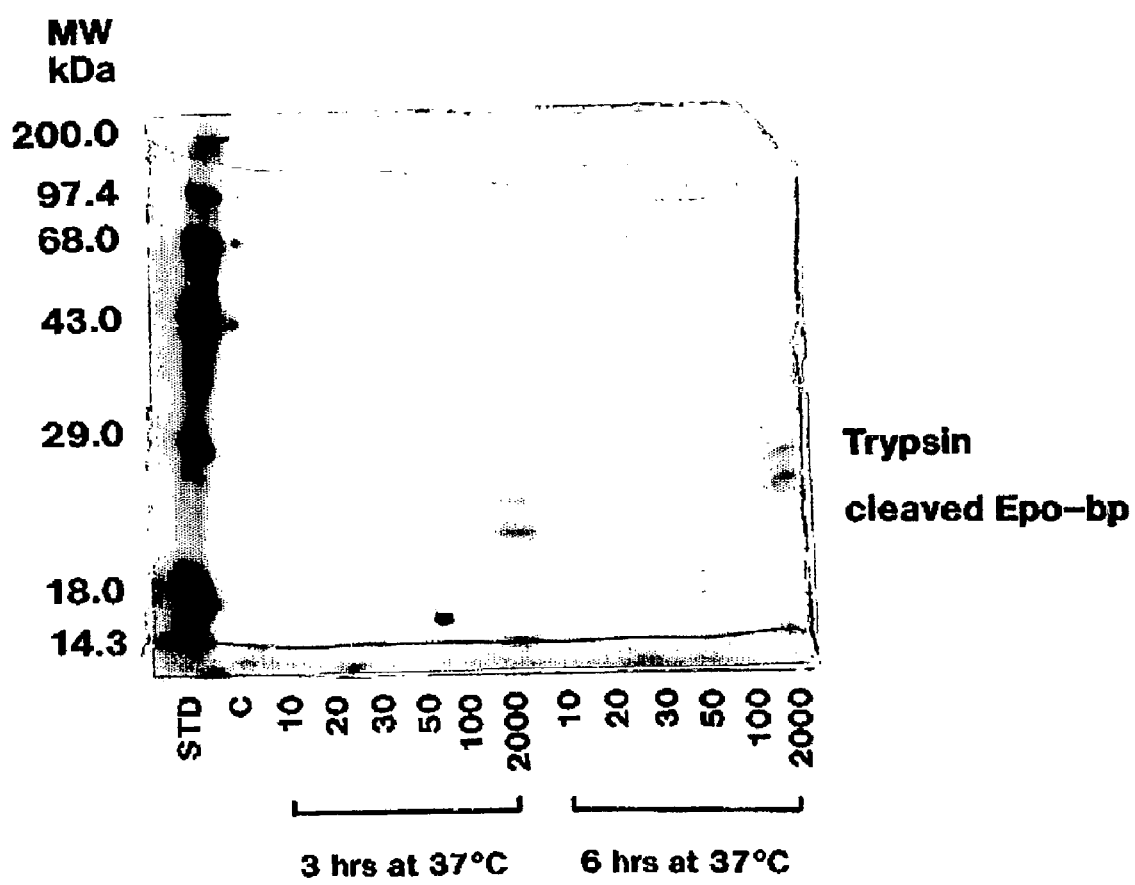
FIG. 6 is a photograph of a Coomassie blue stained polyacrylamide gel showing the polypeptide bands observed after trypsin digestion of Epo-bp.
Figure 8A:
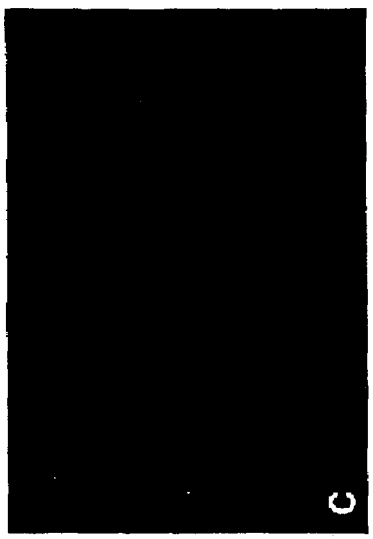
FIGS. 8A-8F are photomicrographs of control bone marrow cells with or without fluorescein labeling.
Figure 8B:
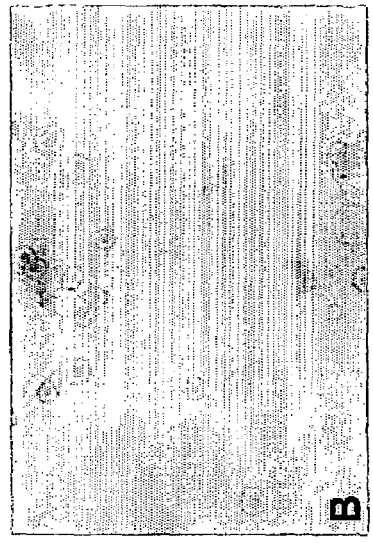
Figure 8C:
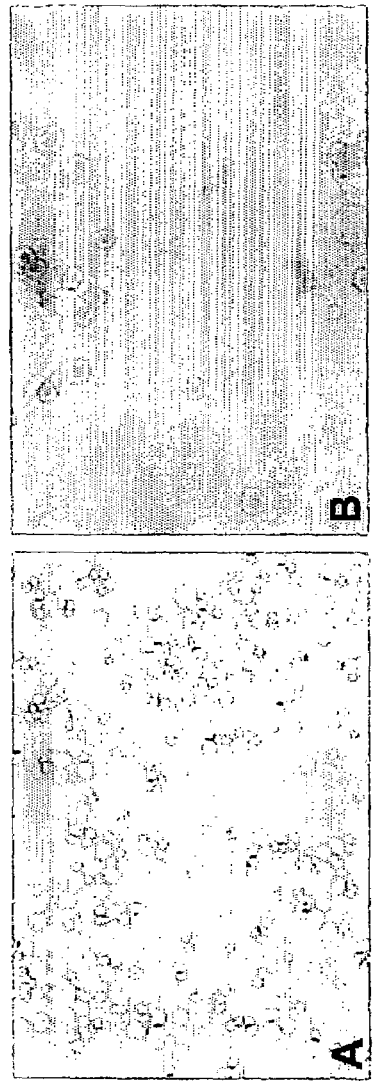
Figure 8D:
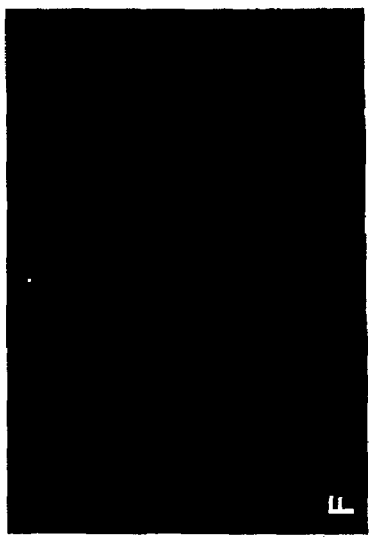
Figure 8E:
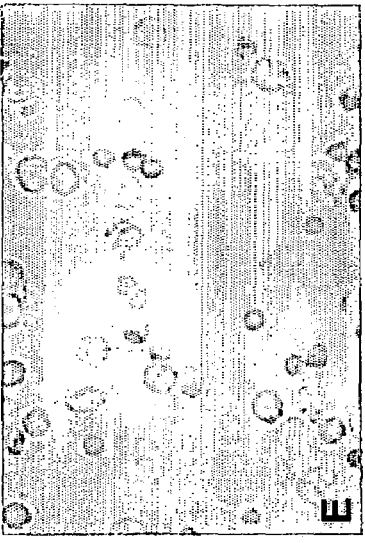
Figure 8F:
Figure 9A:
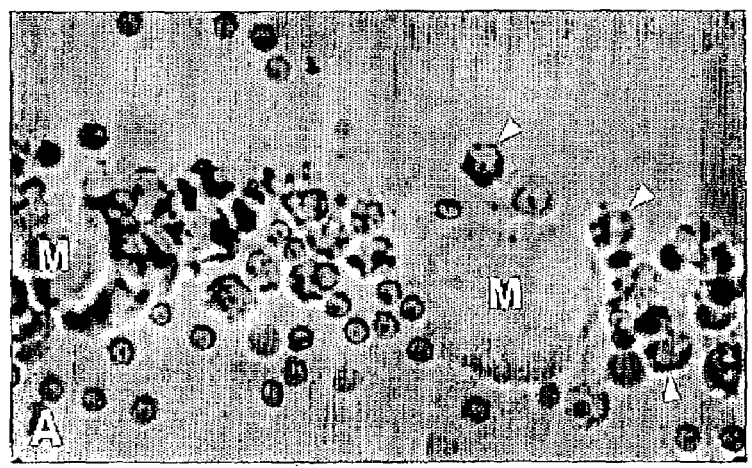
FIGS. 9A-9F are photomicrographs of fluorescein labeled receptor sites of bone marrow progenitor cells. M: Megakaryocytes; ∗Basophil erythroblast; ▶Polychromatophil erythroblast; ⊲Myeloblast; ⇔Normoblast (Magnification: A and B: 400×; C-F: 1000×).
Figure 9C:
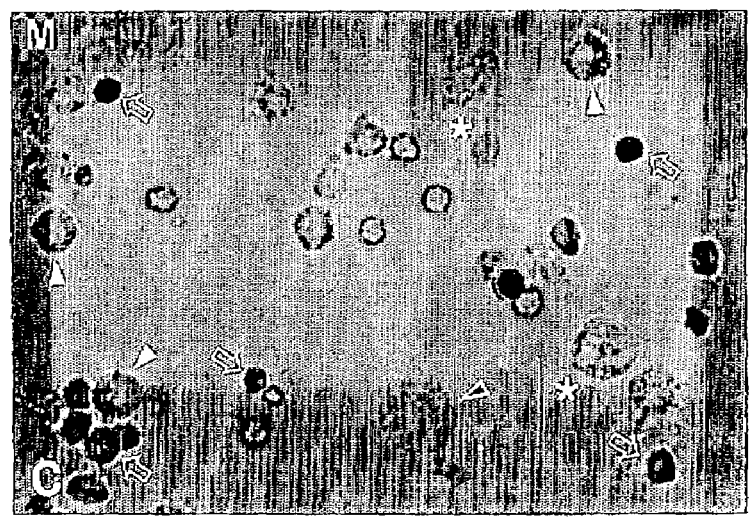
Figure 9E:
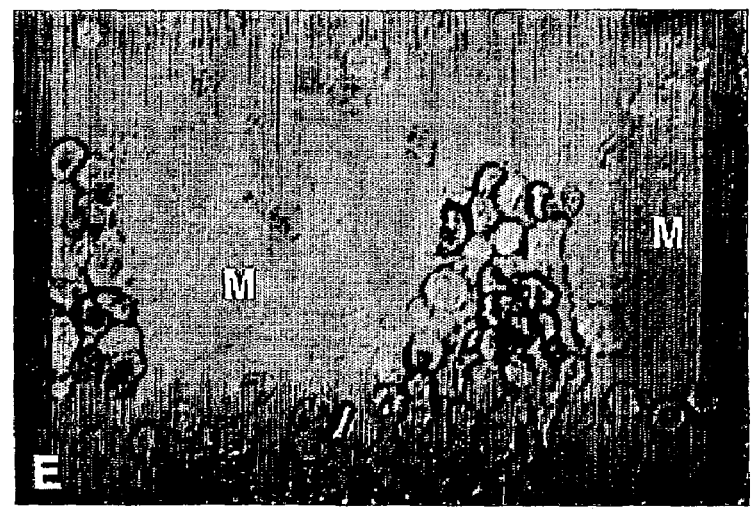
Figure 9B:
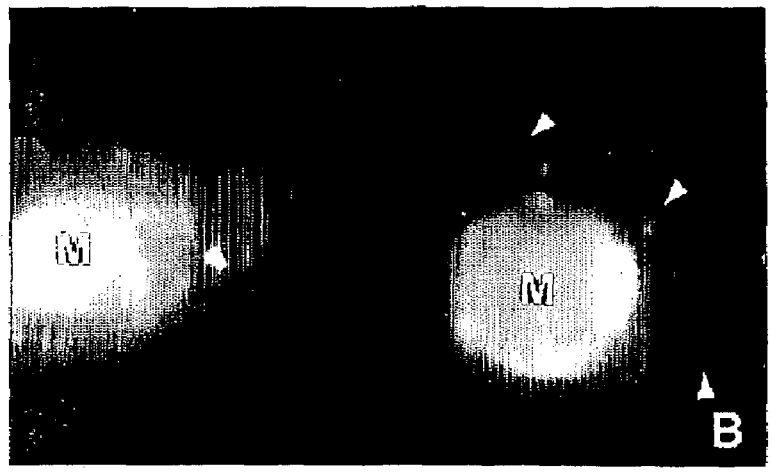
Figure 9D:
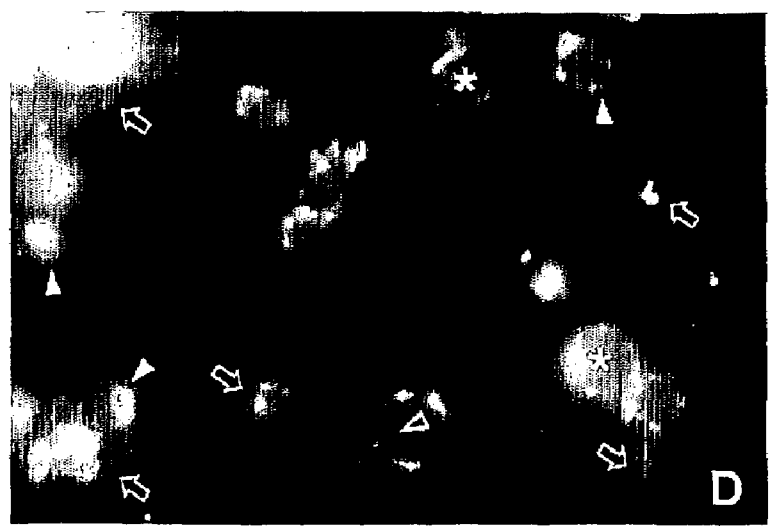
Figure 9F:
Figure 10A:
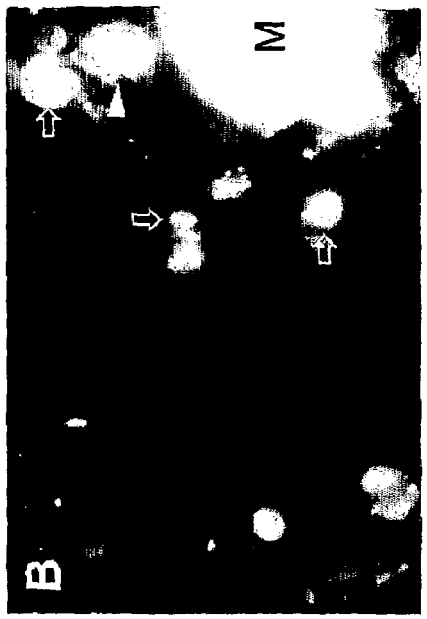
FIG. 10 are photomicrographs of the same cell preparation as FIG. 9 with a different site set up. M: Megakaryocytes; ∗Basophil erythroblast; ▶Polychromatophil erythroblast; ⇔Normoblast (Magnification: 1000×).
Figure 10B:
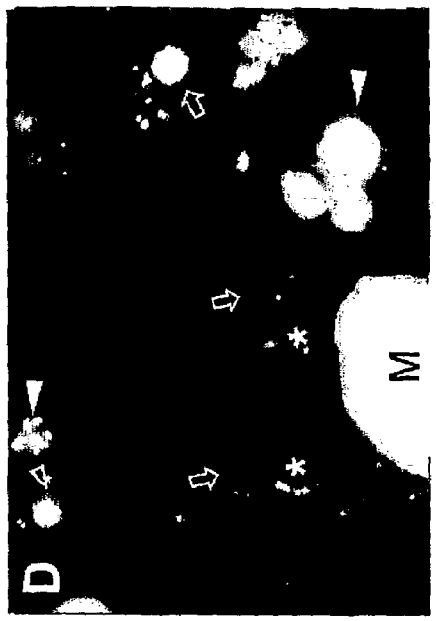
Figure 10C:
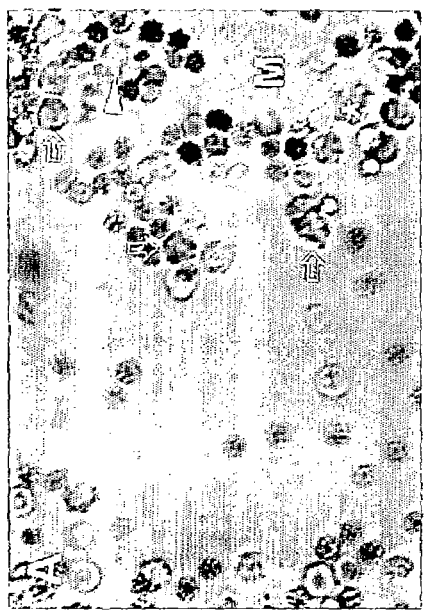
Figure 10D:
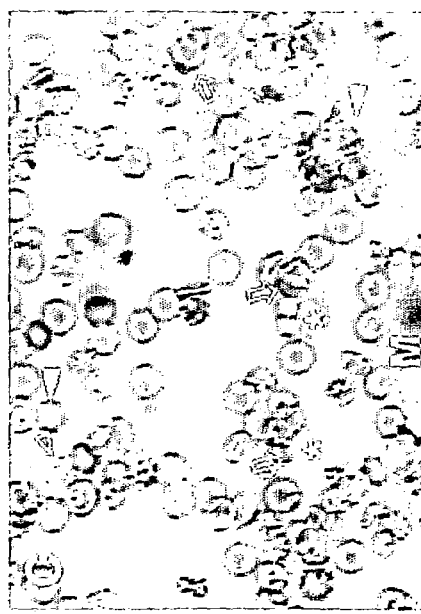

Trypsin digestion experiments were performed to find a minimum sequence of Epo-bp involved in ligand binding. There are several arginine and lysine sites in the Epo receptor protein, which may be specific sites for trypsin digestion. Trypsin digestion of Epo-bp was carried out at 10, 20, 30, 50, 100 µg and 2 mg of trypsin per 5 µg of Epo-bp in a total volume of 200 µg in PBS, pH 6.7 at 37° C. for 3 or 6 hours. The reaction was stopped by adding the same volume of 2N acetic acid or by boiling. As shown in FIG. 6, Epo-bp was cleaved effectively when 20 µg or more of trypsin was present. Trypsin is visible as a 23.2 kDa protein band in the lane having 2 mg of trypsin. The trypsin digested Epo-bp is visible as a 20-kDa protein. In FIG. 6, Lane 1 contains standard molecular weight markers; lane 2 is a control; lanes 3-8 represent digestions at concentrations of 10, 20, 30, 50, 100 µg and 2 mg trypsin, respectively at 37° C. for 3 hours; lanes 9-14 represent the same concentrations of trypsin incubated at 37° C. for 6 hours.

Since uncut Epo-bp is aproximately 30 kDa, gel filtration chromatography using Pharmacia Sephadex G-50 (MW 30,000) was applied to separate protein components of size.ltoreq.30,000 molecular weight from the total mixture. A powdered form of Sephadex G-50 was hydrated and washed several times with isotonic PBS to wash out preservatives. Trypsin digested EpoRex-th was applied to the top of the gel column in a total volume of 0.2 ml in PBS. The column was centrifuged at 2,000×g for 4 min at room temperature in a swinging-bucket rotor. The first effluent was collected from the bottom of the syringe (about 0.2 ml) into a decapped microfuge tube. This effluent contains proteins having a size larger than Epo-bp. Another 0.2 ml of PBS buffer was added to the column and a second eluate collected into a new decapped microfuge by recentrifuging for 10 min. This step was repeated twice. The second eluate was applied to an Epo-agarose column and peak fractions were examined by SDS-PAGE gels and Western blotting. The final product of Epo-bp, as a result of trypsin digestion, was approximately 20 kDa, shown in FIG. 6. The antibody did not recognize the cleaved Epo-bp. Thus, deletion of 30 amino acids from Epo-bp by trypsin digestion completely eliminated recognition by antibodies to Epo-bp, as verified by Western blotting.

Example 7

Detection of EpoR in Progenitor Cells

PCR reagents were purchased from Perkin-Elmer Cetus Norwalk, Conn.) and Affigel® 15 from BioRad (Hercules, Calif.). Isopropylthio-D-galactoside (IPTG) was purchased from BRL Gibco (Rockville, Md.). Nitrocellulose was purchased from Schleicher & Schuell co. (Keene, N.H.). Chemiluminescence (ECL) reagents were purchased from Amersham (Arlington Heights, Ill.). 2,7-Dichlorofluoresein, Phenylmethylsulfonyl-fluoride (PMSF), diisopropylfluorophosphate (*DFP), thrombin, Triton X-100, biotin-amidocaproyl hydroazide, alkaline phosphatase conjugate, and disodium p-nitrophenyl phosphate were purchased from Sigma Chemical Co. (St. Louis, Mo.). Biotinylated rabbit anti-sheep antibodies, avidin-horseradish peroxidase, and IgG purification kits were purchased from Pierce Chemical Co. (Rockford, Ill.). Digoxigenin (for labeled nucleic acids), streptavidin and rabbit anti-digoxigenin Fab/alkaline phosphate conjugates were purchased from Boehringer Manheim Corp. (Indianapolis, Ind.), and microplates were purchased from Corning Costar (Cambridge, Mass.). Sheep anti-Epo and anti-Epo-bp antibodies were prepared as described above in Example 5. Oligonucleotides were synthesized by the microchemical facility of the Institute of Human Genetics, University of Minnesota, Minneapolis, Minn. All other chemicals were of reagent grade.

Animals: Five week old male Sprague-Dawley rats were assigned into control or Epo treatment groups with a light (L) cycle from 04:00 to 18:00 and with each subgroup of five rats at 0, 4, 8, 12, 16, and 20 hours after L-on. Rats were on a standard rat chow and had freely accessible drinking water. After four weeks, body weight was measured every four hours just before and immediately after the completion of a four-week course of three times-weekly Epo (50-U/kg BW)

or physiological saline injections. For blood pressure measurement, the rat's femoral artery was canulated.

Statistical Method: Results were analyzed by the two-tailed Student t-test, and linear least squares rhythmometry. Data are expressed as mean±SEM. A p value of less than 0.05 was considered significant.

Results: Every rat treated with 50 units/kg Epo, three times weekly for four weeks, exhibited splenomegaly (120 rats), while none of the saline treated rats exhibited splenomegaly. It should be noted that the concentration used in the current study fell within the dose commonly used in clinical settings (50-150 units/kg). FIGS. 7A-7C are representative of Epo treated spleens, while FIG. 7D is a control spleen. Blood pressures were elevated overall with Epo treatments. Baseline values of control vs. Epo treatment were 89 vs. 86 mm Hg, whereas post treatment values were 116 vs. 135 mm Hg (p<0.0001). At the given values of blood pressure elevation, increased hematocrit, and spleen enlargement, the changes were worse in the early morning (8:00 a.m. values, the worst for all the three). Table 1 provides a summary of the observations.

The receptor was labeled by the following method. Bone marrow cells were washed three times in PBS and dispensed at $1\text{-}3\times10^3$ cells per well of round-bottomed microplates for control and samples. Supernatants were removed and 100 µl of purified Fab-fractionated fluorescein conjugated anti-Epo-bp antibodies were added. The mixture was incubated on ice for 30 minutes, and then cells were washed three times by adding 400 µl of buffer containing 1% FCS and 0.01% $NaN_3$ in PBS to each sample and centrifuged at 200 g for two minutes. The cells were resuspended onto a vortex in total volume up to 50 µl of PBS and analyzed under an inverted fluorescence microscope. FIGS. 8A-8F are photomicrographs of control bone marrow cells with or without fluoroscein labeling. FIGS. 9A-9F are photomicrographs of bone marrow progenitor cells with or without fluorescein labeling. The binding site of the receptor is visualized using the fluorescent labeling technique. It should be noticed that the binding sites are located among the megakaryocytes (M), erythroblasts (*, ▶), and normoblasts (⇔) as well as myeloblasts (◁). FIG. 10 contains the same preparation as FIG. 9, except that a different field is shown. This is the first publication showing the cell receptor site among the cells and identifying the cell type where the receptor is located.

TABLE 1

Circadian variations of body weight, blood pressure and hematocrit with Epo treatment

| Variable | Time | Rats (n) | Control | EPO treatment | p-value |
|---|---|---|---|---|---|
| Body weight (g) | 0000 | 5 | 313 ± 11.6 | 305 ± 13.0 | ns |
| | 0400 | 5 | 305 ± 8.9 | 294 ± 6.7 | ns |
| | 0800 | 5 | 324 ± 18.4 | 294 ± 4.9 | ns |
| | 1200 | 5 | 308 ± 13.0 | 290 ± 9.0 | ns |
| | 1600 | 5 | 310 ± 10.2 | 295 ± 13.9 | ns |
| | 2000 | 5 | 317 ± 13.3 | 291 ± 14.3 | ns |
| BP(mm Hg) | 0000 | 5 | 116 ± 5.8 | 131 ± 7.6 | ns |
| | 0400 | 5 | 120 ± 4.6 | 131 ± 4.8 | ns |
| | 0800 | 5 | 116 ± 5.8 | 139 ± 3.9 | 0.003 |
| | 1200 | 5 | 108 ± 1.0 | 128 ± 8.1 | 0.041 |
| | 1600 | 5 | 119 ± 3.2 | 140 ± 6.3 | 0.016 |
| | 2000 | 5 | 118 ± 4.1 | 137 ± 6.2 | 0.030 |
| Hematocrit (%) | 0000 | 5 | 42 ± 2.6 | 60 ± 4.5 | 0.009 |
| | 0400 | 5 | 41 ± 2.3 | 64 ± 2.2 | <0.0001 |
| | 0800 | 5 | 42 ± 1.6 | 66 ± 2.7 | <0.0001 |
| | 1200 | 5 | 44 ± 0.5 | 65 ± 1.5 | <0.0001 |
| | 1600 | 5 | 45 ± 1.4 | 61 ± 3.8 | 0.003 |
| | 2000 | 5 | 43 ± 3.0 | 64 ± 1.5 | 0.001 |
| Spleen Weight (g) | 0000 | 5 | 0.83 ± 0.2 | 1.63 ± 0.5 | 0.01 |
| | 0400 | 5 | 0.82 ± 0.2 | 1.47 ± 0.7 | ns |
| | 0800 | 5 | 0.88 ± 0.1 | 1.69 ± 0.2 | <0.0001 |
| | 1200 | 5 | 0.96 ± 0.2 | 1.63 ± 0.3 | 0.004 |
| | 1600 | 5 | 0.73 ± 0.1 | 1.37 ± 0.4 | 0.004 |
| | 2000 | 5 | 0.92 ± 0.2 | 1.60 ± 0.6 | 0.03 |

Legend:
n = number;
ns = statistically not significant;
BP = blood pressure

Example 8

Immunofluorescent Labeling Method for Detecting Epo or EpoR or Portions Thereof

Fluorescent labeling of Epo/Epo-bp and their antibodies was carried out according to manufacturer's instructions. The Fab antibody fraction that was fluorescein-labeled also was purified as described in the manufacturer's protocol. The Fc fraction also can be purified and saved for other uses. These materials were used to detect Epo and EpoR in blood and/or tissue samples, including plasma, serum, megakaryocytes, RBC and WBC progenitors, or homogenized spleen or kidney samples. PBS containing 16 mM $Na_2HPO_4$, 4 mM $NaH_2PO_4$ and 2.7 mM KCl in 0.9% NaCl, pH 7.4 was used unless otherwise indicated. Assay results can be ready in less than one hour.

A. Serum/Plasma/Homogenized Tissue Samples

Precoat a 96-well microplate with 1 µg/well of purified anti-Epo antibodies for Epo or anti-Epo-bp antibodies for Epo-bp or EpoR detection. Anti-epo and anti-Epo-bp antibodies are precoated on the 96-well microplate in different, discrete regions to facilitate simultaneous detection of Epo and EpoR.

1) Add 200 µl of 1:10 diluted sample (serum/plasma/homogenized tissue) to capture Epo/antibodies or Epo-bp/antibodies. The mixture is incubated at 37° C. for 20 minutes then supernatant is removed by inverting the plate with a single flicking motion over a sink.

2) Add 100 µl/well of 1 µg/ml Fab-fractionated fluorescein labeled anti-Epo antibodies for Epo, or Fab-fractionated fluorescein labeled anti-Epo-bp antibodies for Epo-bp or EpoR detection, and fluorescein labeled Epo or Epo-bp for anti-Epo or anti-Epo-bp antibody detection, respectively. Incubate the mixture at 37° C. for 15 minutes and wash three times with 400 µl/well of buffer containing 1% FCS and 0.01% $NaN_3$ in PBS.

3) Add 50 µl of PBS buffer and analyze under an inverted fluorescence microscope and/or measure the absorbance at 490 nm using a microplate fluorometer.

B. Progenitor Cell Samples

1) Washed blood or bone marrow cells in PBS are dispensed at $1\text{-}3\times10^3$ cells per well of a round-bottomed microplate for control and sample plates, and centrifuged into a pellet at 200 g for two minutes using a microtiter plate rotor attached centrifuge.

a. Remove supernatants and add 100 µl of Fab-fractioned fluorescein conjugated antibodies, and mix plate well onto a vortex. Incubate the mixture on ice for 30 minutes, and then wash cells three times by adding 400 µl of buffer containing 1% FCS and 0.01% $NaN_3$ in PBS to each well and centrifuged at 200 g for two minutes.

b. Resuspend the cells in the plate onto a vortex in total volume up to 50 µl of PBS and analyze under an inverted fluorescence microscope and/or measure the absorbance at 490 nm using a microplate fluorometer.

Fluorescein labeled cells can be analyzed immediately or kept on ice for up to two to three hours. FIGS. 9 and 10 show the fluorescein labeled receptor sites of bone marrow progenitor cells where the receptor is visualized.

Example 9

PCR Method of Detection

Colorimetric substrate and antibodies will be used to detect ligand-binding sites and to measure Epo/Epo-R mRNA productions. For rapid labeling to develop an enzyme immunoassay, nonradioactive labeling of PCR generated probes with Epo/Epo-R DNA can be applied in hybridization to reduce nonspecific background reactions reflecting cross-hybridization between vector sequences. For ELISA-type detection of DIG modification with digoxigenin-specific alkaline phosphatase (AP) conjugates, the PCR product can be used as nonradioactive hybridization probe and, unlabeled target nucleic acid is hybridized to make DIG-labeled hybridization complex. Antigen-antibody-AP complexes are located using the substrate 5-bromo-4-chloro-3-indolyl phosphate (BCIP) in combination with nitro blue tetrazolium chlorida (NBT), which detects the precipitated inoxyl group.

mRNA Extraction: Total RNA was extracted using total RNA kits from Qiagen Inc. (Chatsworth, Calif.), with equal weight of each organ or equal cell numbers (use 2 ml of blood sample to lyse or 1 gram of tissue to homogenize for RNA extraction, according to the manufacturer's description). Samples were prepared to adjust binding conditions and applied to RNeasy Kit, and washed three times with PBS to elute total RNA. mRNA will be purified using a Perkin-Elmer Cetus PCR kit with Epo or Epo-R primers and the total RNA from the above extracted sample. The mRNAs were verified on an agarose gel stained with ethidium bromide. The mRNA bands are read/quantitated and documented with photographs.

Stock Solutions:
  BCIP: 50 mg/ml 10% dimethlyformide;
  NBT: 50 mg/ml, 70% dimethylformamide, stored in the dark, 4° C.;
  Alkaline phosphatase (AP): nitroblue tetrazolium chloride (20 µl at 50 mg/ml in 50% dimethylformamide) and 5-bromo-4-chloro-3-indoyl phosphate p-toluidine salt (100 µl at 50 mg/ml 50% dimethylformamide) are dissolved in 30 ml of 100 mM Tris-Cl, pH 9.5, 100 mM NaCl, 5 mM $MgCl_2$ stored at room temperature.
  BCIP/NBT preparation: just before use, add 33 µl of NBT stock solution to 5 ml of ALP buffer and mix well. Then, add 16.5 µl of BCIP stock solution and mix well. The substrate mixture should be used within 30 minutes.

For optical detection, the optical substrates BCIP/BT are added, resulting in blue color products and measured the absorbance at 405 nm.

Procedure:
1) A PCR kit is provided that includes control template, a pair of Epo and Epo-R PCR primers, Taq DNA polymerase, and Digoxigenin-labeled-dUTP/dNTP. Sample DNA is needed when the test is performed. Taq DNA polymerase also can be purchased separately from elsewhere.
2) Twenty-five cycles are PCR are performed to produce Dig-DNA, biotinylated DNA, or Dig-biotinylated DNA fragments in a total volume of 100 µl. PCR products are verified on, for example, by electrophoresis through a 1% agarose gel and ethidium bromide staining.
3) A 96-well EIA microplate is precoated with 100 µl of streptavidin per well (10 µl/ml in TBS, containing 20 mM Tris-HCl, 150 mM NaCl, pH 8.0) for biotinylated DNA detection in the avidin-biotin complex method or purified Epo/EpoR antibodies for either biotinylated or Dig-labeled detection.
4) Volume of PCR products is increased to 200 µl in TBS. Approximately 100 µl of the PCR product is added in duplicate to the 96-well EIA microplates to immobilize. Incubate at 37° C. for 30 minutes to bind PCR products, then supernatants are removed by inverting the plate with a single flicking motion over the sink.
5) Add 100 µl/well of alkaline phosphatase-conjugated rabbit polyclonal sheep anti-digoxigenin Fab (1 µg/ml) and incubate at 37° C. for 30 minutes, then wash three times in 400 µl of TBS.
6) Add 100 µl substrate solution. Phosphatase substrate, disodium p-nitrophenyl phosphate (1 mg/ml) in 10% vol/vol diethanolamine-HCl buffer, pH 9.5, will be added for color development. Incubate at room temperature for 30 minutes for enzyme reaction and then add 100 µl of stop solution containing 0.01% $NaN_3$ and wash three times with 400 µl of TBS (do not shake while color is developing).
7) Record color development visually and determine the absorbance at 405 nm by an ELISA reader.

Digoxigenin-incorporated DNA fragments are recognized by anti-digoxigenin antibodies.

Example 10

Enzyme Immunoassay (EIA) Method

Bead Method
  Epo and Epo-bp agarose beads are prepared with overnight dialyzed Epo and Epo-bp (0.5 mg/ml) in 0.1 M 3(n-morpholino)-propanesulfonic acid (MOPS) at 4° C., and linked to Affigel® 15 beads by admixing 1 ml of the dialyzed Epo or Epo-bp solution and 2 ml of washed Affigel® 15. The mixture was incubated at room temperature for two hours on a rotating shaker. Supernatant was removed after microcentrifuged at 2000×g for 30 seconds, and washed three times in PBS or TBS, depending on the next step.

1) Affigel® 15 beads are coated with 2 µg/well anti-Epo for Epo and vice versa, or anti-Epo-bp antibodies for Epo-bp detection, and vice versa.
2) 200 µl of 1:10 diluted sample serum/plasma/homogenized tissue in TBS is added to capture Epo/antibodies or Epo-bp/antibodies, respectively, then incubated at room temperature for 25 minutes with a gentle rocking and washed three times with TBS at 200 g for two minutes at 4° C. to remove supernatant.
3) 100 µl of 1 µg/ml rabbit anti-sheep immunoglobulins/alkaline phosphatase conjugate is added as an indicator and incubated at room temperature for 25 minutes with gentle rocking and washed three times with TBS.
4) 100 µl of phosphatase substrate, disodium p-nitrophenylphosphate (1 mg/ml) in 10% vol/vol diethanolamine-HCl buffer, pH 9.5, are added for the color development, incubated for 30 minutes at room temperature, and the absorbance at 405 nm measured.

Example 11

Avidin-Biotin Complex Method

Epo, Epo-bp and their antibodies were biotinylated with biotin-amidocaproyl hydroazide according to the manufacturer's instructions. 2.5 mg of each product from chromatography was dialyzed overnight in PBS buffer before the biotinylation. Each dialyzed product was biotinylated by adding 40 mg biotin-amydocaproyl hydrazide and 5 mg NaCNBH$_3$ (Sigma, St. Louis, Mo.), and incubated at 37° C. for two hours. Residual reagents were separated from the products by extensive dialysis in a PBS buffer. Detection includes Epo for anti-Epo antibodies, anti-Epo antibodies for Epo, Epo-bp for anti-Epo-bp antibodies and anti-Epo antibodies for Epo-bp detection in blood and/or tissue samples, including plasma or serum progenitors, and homogenized spleen or kidney samples.
1) A 96-well microplate is precoated with 100 µl of 20 µg/ml in PBS per well of purified anti-Epo for Epo or vice versa; or anti-Epo-bp antibodies for Epo-bp detection or vice versa.
2) 200 µl of 1:10 diluted sample serum/plasma/homogenized tissue are added and incubated at 37° C. for 30 minutes and then supernatant is removed.
3) 100 µl of 10 µg/ml in PBS per well of biotinylated anti-Epo for Epo or vice versa or anti-Epo-bp antibodies for Epo-bp detection or vice versa. The mixture is incubated at 37° C. for 20 minutes, then washed three times with 400 µl PBS.
4) 100 µl of streptavidin (2 µg/ml) per well in PBS buffer is added and incubated at 37° C. for 20 minutes, then washed three times with PBS containing 1% FCS and 0.01% NaN$_3$. The supernatant is removed by inverting the plate with a single flicking motion over a sink.
5) The mixtures in the plate are resuspended by vortexing in a total volume up to 100 µl of the buffer and the absorbance is measured at 405 nm using a BioRad microplate reader or any equivalent microplate reader. Assay results can be ready in less than one hour.

Primary antibodies locate target proteins, which are detected by using species-specific secondary antibodies to conjugate with horseradish peroxides (HRP). HRP-conjugated streptavidin complexes can also be used without changes to routine protocols. HRP-conjugated molecules (e.g., antibodies, sreptavidin or protein A) will catalize the oxidation of Luminol and detect light emission via chemiluminescence that can be enhanced by the sustained emission of light provided by the inclusion of chemical enhancers in the HRP-catalized oxidation of Luminol. ECL gives approximately 1000-fold more light than the oxidation of Luminol alone.

Example 12

EIA for Detection of Epo and EpoR

Blood samples were obtained from volunteers at the University of Minnesota laboratories, Twin Cities hospitals and blood bank, as well as from Japanese Hospitals in Yokohama and Tokyo. All antibodies and Epo-bp were prepared as described above. The EIA was performed as follows.
1) EIA microplates were coated with 2 µg/well anti-Epo for Epo or anti-Epo-bp antibodies for Epo-bp detection. For antibody detection, plates were coated with 200 µl of 1:10 diluted serum or plasma in PBS, pH 7.4 and incubated at room temperature for 30 min or stored at 4° C. overnight.
2) Wells were washed 3 times with 200 µl/well PBST (0.05% Tween 20 (Sigma Chemical Co., MO) in PBS).
3) Nonspecific binding sites were blocked by adding 200 µl 1% BSA in PBST to each well and incubating for 30 min at room temperature.
4) Wells were washed 3 times with 200 µl/well PBST.
5) Streptavidin (2 µg/well in 200 µl PBST) labeled antibodies (Fab anti-Epo-antibody for Epo, Epo for Epo antibody, Fab anti-Epo-bp antibody for Epo-bp or Epo-bp for anti-Epo-bp antibody detection) were added to wells and samples were incubated at room temperature for 30 min.
6) Wells were washed 3 times with 200 µl/well PBST.
7) To each well, 160 µl of O-Phenylene-Diamine Dihydrochloride (oPD) (Sigma Chemical Co., MO) in Phosphate-Citrate buffer, pH 6, were added and incubated for 30 min at room temperature.
8) The reaction was stopped by adding 40 µl 5N NaOH and the absorbance was measured at 405 nm.

oPD in phosphate citrate buffer was prepared as follows. For 100 ml, 4.86 ml 0.5 M Citrate, 10.28 ml 0.5 M Na$_2$HPO$_4$, 2 ml oPD stock (10 mg/ml) and up to 100 ml in dH$_2$O, pH 6.0. Immediately before use, 400 µl of 3% H$_2$O$_2$ were added.

Figure 11:
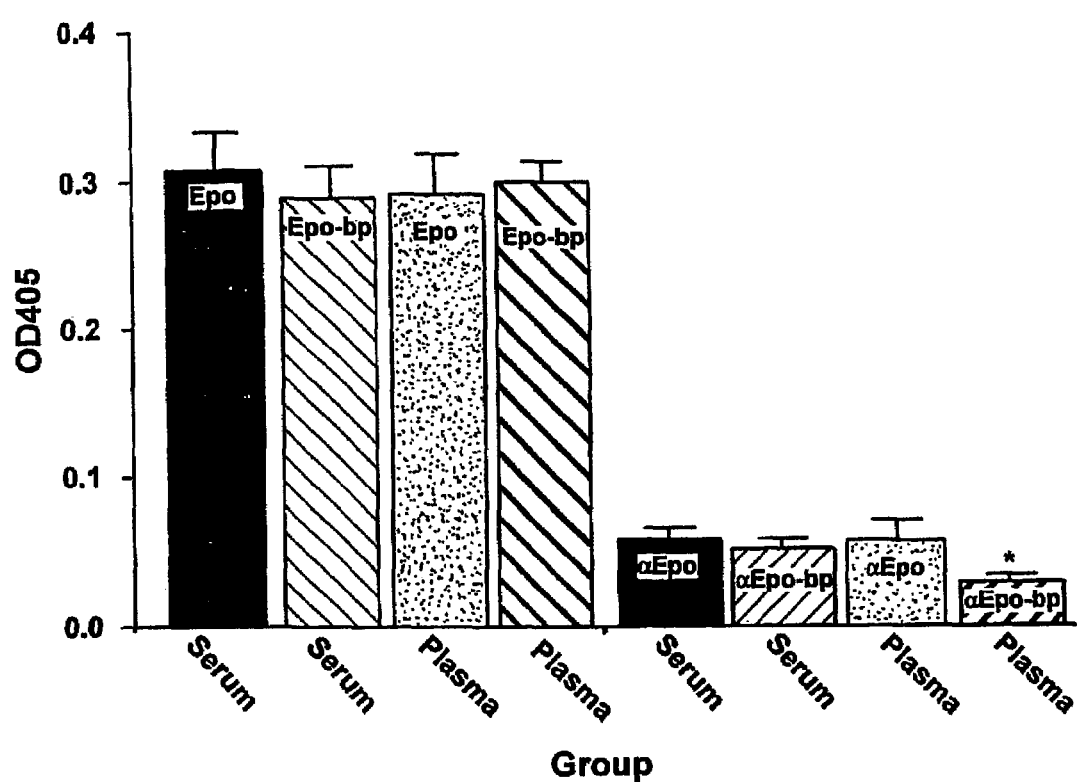
FIG. 11 is a graph of optical density (405 nm) of Epo and Epo-bp in serum or plasma samples. Error bars represent standard error (SE).

The results of the EIA are presented in FIG. 11, in which optical density (OD) of each measurement is presented as the mean±SE of 8-14 individual samples (in duplicates). The OD measurements presented in FIG. 11 were calculated by subtracting the OD value of the blanks from the OD of each sample. As shown in FIG. 11, OD of Epo and Epo-bp in serum and plasma are similar to each other (OD$_{405}$: 0.308±0.026, 0.289±0.022, 0.289±0.028 and 0.299±0.015 for serum Epo, serum Epo-bp, plasma-Epo and plasma-Epo-bp, respectively). The plasma level of anti-Epo-bp antibody level was significantly lower than that of the other three categories: 0.058±0.008; 0.052±0.006; 0.054±0.013; and 0.031±0.004 for serum anti-Epo, serum anti-Epo-bp, plasma anti-Epo and plasma anti-Epo-bp, respectively ($p<0.025$). Antibodies against Epo or Epo-bp in serum and Epo in plasma appeared to be similar. The Epo and Epo-bp values were converted with known Epo concentrations prepared as controls in the same plate to mU/ml. In serum 25.4±2.17 mU/ml of Epo and 24.2±1.84 mU/ml of Epo-bp were present. In plasma, 24.2±2.35 mU/ml of Epo and 25.0±1.26 mU/ml Epo-bp were present.

This assay is a simple method for measuring Epo and Epo-bp and provides a more sensitive assay than measuring Epo and Epo-bp by radioimmunoassay (17.7±6.3 mU/ml) in terms of unit numbers and much smaller SE. Furthermore, the materials used in the preparation are environmentally friendly as compared with materials used in the conventional methods, such as radioactive or other toxic chemicals.

The foregoing detailed description has been provided for a better understanding of the invention only and no unnecessary limitation should be understood therefrom as some modifications will be apparent to those skilled in the art without deviating from the spirit and scope of the appended claims.

What is claimed:

1. A method for simultaneous measurement of erythropoietin (Epo) and Epo receptor (EpoR) in a biological sample, said method comprising:
   a) providing a solid substrate having first and second antibodies attached thereto in different and discrete regions, wherein said first antibody has specific binding affinity for Epo and said second antibody has specific binding affinity for EpoR, and wherein said first and second antibodies are functional antibody fragments;
   b) contacting said solid substrate with said biological sample under conditions wherein Epo and EpoR in said biological sample becomes bound to said first and said second antibodies; and
   c) detecting the presence, absence, or amount of Epo and EpoR on said solid substrate.

2. The method of claim 1, wherein said functional antibody fragments are Fab fragments.

3. The method of claim 1, wherein said first and second antibodies are polyclonal antibodies.

4. The method of claim 1, wherein said detecting the presence, absence, or amount of Epo and EpoR comprises contacting said solid substrate of part b) with third and fourth antibodies, wherein said third antibody has specific binding affinity for Epo and said fourth antibody has specific binding affinity for EpoR, and wherein said third and fourth antibodies are detectably labeled.

5. The method of claim 4, wherein said third and fourth antibodies are polyclonal antibodies.

6. The method of claim 1, wherein said detecting the presence, absence, or amount of Epo and EpoR comprises:
   d) contacting said solid substrate of part b) with third and fourth antibodies, said third antibody having specific binding affinity for Epo and said fourth antibody having specific binding affinity for EpoR; and
   e) contacting said solid substrate of part d) with fifth labeled antibodies having specific binding affinity for said third and fourth antibodies.

7. The method of claim 6, wherein said third and fourth antibodies are polyclonal antibodies.

8. The method of claim 6, wherein said fifth labeled antibodies are labeled with an enzyme, a substrate, or a fluorescent moiety.

9. The method of claim 1 wherein the second antibody has specific binding affinity for Epo-bp fragment of EpoR.

10. The method of claim 1 wherein the solid substrate further comprises third and fourth different and discrete regions, different and discrete from the regions with the first and second antibodies attached thereto, wherein the method further comprises:
   d) contacting the third discrete region of the solid substrate with the biological sample under conditions wherein anti-Epo antibodies become bound to the solid substrate in the third discrete region; and
   e) contacting the fourth discrete region of the solid substrate with the biological sample under conditions wherein anti-EpoR antibodies become bound to the solid substrate in the fourth discrete region; and f) detecting the presence, absence, or amount of anti-Epo antibodies on said solid substrate in the third discrete region; and g) detecting the presence, absence, or amount of anti-EpoR antibodies on said solid substrate in the fourth discrete region.

11. The method of claim 10 wherein steps d) and e) comprise contacting the third and fourth discrete regions of the solid substrate with the biological sample under conditions wherein antibodies in the biological sample become bound to the solid substrate in the third and fourth discrete regions;

step f) comprises contacting the third discrete region with Epo under conditions wherein the Epo becomes bound to any anti-Epo antibody bound to the solid substrate, and detecting the presence, absence, or amount of Epo on said solid substrate in the third discrete region; and step g) comprises contacting the fourth discrete region with Epo-bp under conditions wherein the Epo-bp becomes bound to any anti-Epo-bp antibody bound to the solid substrate, and detecting the presence, absence, or amount of Epo-bp on said solid substrate in the fourth discrete region.

12. A kit for detecting Epo and EpoR in a biological sample, said kit comprising:

(a) a solid substrate having first and second antibodies attached thereto in different and discrete regions, wherein said first antibody has specific binding affinity for Epo and said second antibody has specific binding affinity for EpoR, and wherein said first and second antibodies are functional antibody fragments;

(b) a first container having third antibodies enclosed therein, wherein said third antibodies have specific binding affinity for Epo; and (c) a second container having fourth antibodies enclosed therein, wherein said fourth antibodies have specific binding affinity for EpoR.

13. The kit of claim 12, wherein said kit further comprises a third container having control antigen enclosed therein.

14. The kit of claim 12, wherein said kit further comprises a label or package insert indicating that Epo and EpoR can be simultaneously detected by contacting said solid substrate with said biological sample under conditions wherein any Epo or EpoR in said biological sample becomes bound to said first and second antibodies and contacting said solid substrate with Epo or EpoR bound thereto with said third and said fourth antibodies.

15. The kit of claim 12, wherein said first and second antibodies are polyclonal antibodies.

16. The kit of claim 12, wherein said first and second antibodies are functional antibody fragments.

17. The kit of claim 12, wherein said third and fourth antibodies are polyclonal antibodies.

18. The kit of claim 12, wherein said solid substrate is a microtiter plate.

19. The kit of claim 12 wherein the second antibody and the fourth antibody have specific binding affinity for Epo-bp fragment of EpoR.

* * * * *

SEQUENCE LISTING

<160> NUMBER OF SEQ ID NOS: 3

<210> SEQ ID NO 1
<211> LENGTH: 23
<212> TYPE: DNA
<213> ORGANISM: Artificial sequence
<220> FEATURE:
<223> OTHER INFORMATION: BamH1 linker followed by sequence complementary
      to coding sequence for amino acids 25-29 of human EpoR protein

<400> SEQUENCE: 1
ttggatccgc gccccgcct aac                                             23

<210> SEQ ID NO 2
<211> LENGTH: 22
<212> TYPE: DNA
<213> ORGANISM: Artificial sequence
<220> FEATURE:
<223> OTHER INFORMATION: EcoR1 linker followed by sequence complementary
      to coding sequence for a segment of human EpoR protein

<400> SEQUENCE: 2
tgaattcggg gtccaggtcg ct                                             22

<210> SEQ ID NO 3
<211> LENGTH: 18
<212> TYPE: DNA
<213> ORGANISM: Homo sapiens

<400> SEQUENCE: 3
ctggttccgc gtggatcc                                                  18